(12) United States Patent
Sauer et al.

(10) Patent No.: US 12,251,087 B2
(45) Date of Patent: Mar. 18, 2025

(54) DEVICE FOR VESSEL HARVESTING

(71) Applicant: LSI Solutions, Inc., Victor, NY (US)

(72) Inventors: Jude S. Sauer, Pittsford, NY (US); Matthew David DeClerck, Greece, NY (US)

(73) Assignee: LSI Solutions, Inc., Victor, NY (US)

( * ) Notice: Subject to any disclaimer, the term of this patent is extended or adjusted under 35 U.S.C. 154(b) by 562 days.

(21) Appl. No.: 16/992,804

(22) Filed: Aug. 13, 2020

(65) Prior Publication Data

US 2021/0045766 A1  Feb. 18, 2021

Related U.S. Application Data

(60) Provisional application No. 62/981,813, filed on Feb. 26, 2020, provisional application No. 62/916,571, filed on Oct. 17, 2019, provisional application No. 62/886,374, filed on Aug. 14, 2019.

(51) Int. Cl.
*A61B 17/00* (2006.01)
*A61B 17/32* (2006.01)

(52) U.S. Cl.
CPC .. *A61B 17/00008* (2013.01); *A61B 17/00234* (2013.01); *A61B 17/32002* (2013.01); *A61B 2017/00252* (2013.01); *A61B 2017/320032* (2013.01); *A61B 2017/320044* (2013.01)

(58) Field of Classification Search
CPC ........ A61B 17/00008; A61B 17/00234; A61B 17/32002; A61B 2017/320044
See application file for complete search history.

(56) References Cited

U.S. PATENT DOCUMENTS

| | | | |
|---|---|---|---|
| 5,084,022 A | 1/1992 | Claude | |
| 5,431,639 A | 7/1995 | Shaw | |
| 5,860,923 A | 1/1999 | Lenker et al. | |
| 5,913,866 A | 6/1999 | Ginn et al. | |

(Continued)

FOREIGN PATENT DOCUMENTS

| | | |
|---|---|---|
| DE | 102009011205 | 9/2010 |
| JP | 20140511734 | 5/2014 |

(Continued)

OTHER PUBLICATIONS

Extended European Search Report for Application No. 20852461.1, dated Jun. 15, 2023, 9 pages.

(Continued)

*Primary Examiner* — Sarah A Long
(74) *Attorney, Agent, or Firm* — Michael E. Coyne

(57) ABSTRACT

A device for vessel harvesting is disclosed. The device for vessel harvesting includes a distal housing, a dissector coupled to the distal housing, a drive element coupled to the dissector, and an actuator coupled to the drive element. The device for vessel harvesting may also include a rotatable dissector, a shaft coupled to the distal housing having a first articulation joint movable within a first plane, and a second articulation joint movable within a second plane, which is substantially perpendicular to the first plane, a barrel chain drive element coupled to the rotatable dissector, and an actuator coupled to the drive element. The device for vessel harvesting may also include a member slidably engaged to the distal tip.

18 Claims, 24 Drawing Sheets

(56) References Cited

U.S. PATENT DOCUMENTS

| | | |
|---|---|---|
| 6,084,941 A | 7/2000 | Stenstrom |
| 6,097,978 A | 8/2000 | Demarais et al. |
| 7,258,694 B1 | 8/2007 | Choi et al. |
| 10,420,537 B2 | 9/2019 | Salahieh et al. |
| 2002/0161424 A1 | 10/2002 | Rapacki et al. |
| 2003/0167071 A1 | 9/2003 | Martin et al. |
| 2003/0181907 A1* | 9/2003 | Lindsay ............... A61B 18/148 606/49 |
| 2005/0222499 A1 | 10/2005 | Banik et al. |
| 2006/0149165 A1 | 7/2006 | Kennedy, II et al. |
| 2006/0212107 A1 | 9/2006 | Case et al. |
| 2006/0282117 A1 | 12/2006 | Berberich et al. |
| 2008/0255475 A1 | 10/2008 | Kondrosky et al. |
| 2010/0114301 A1 | 5/2010 | Heaton, II et al. |
| 2010/0222786 A1 | 9/2010 | Kassab |
| 2011/0213347 A1 | 9/2011 | Lee et al. |
| 2012/0109186 A1 | 5/2012 | Parrott et al. |
| 2012/0203240 A1 | 8/2012 | Delahoussaye et al. |
| 2013/0282009 A1* | 10/2013 | Knodel ............... A61B 18/1482 606/47 |
| 2014/0018834 A1 | 1/2014 | Kather et al. |
| 2014/0052061 A1 | 2/2014 | Weisshaupt et al. |
| 2016/0367279 A1 | 12/2016 | Orphanos et al. |
| 2017/0000483 A1* | 1/2017 | Motai ............... A61B 17/07207 |
| 2017/0021139 A1 | 1/2017 | Bajema et al. |
| 2017/0100136 A1 | 4/2017 | Dougherty et al. |
| 2017/0281293 A1 | 10/2017 | Verstege et al. |
| 2017/0281302 A1 | 10/2017 | Pell et al. |
| 2018/0098820 A1 | 4/2018 | Park |
| 2018/0099125 A1 | 4/2018 | Richer et al. |
| 2018/0368965 A1 | 12/2018 | Janardhan et al. |
| 2019/0110788 A1* | 4/2019 | Lombardo ......... A61B 17/0482 |
| 2019/0231528 A1 | 8/2019 | MacMahon et al. |
| 2020/0163713 A1 | 5/2020 | Hatcher et al. |
| 2020/0337726 A1 | 10/2020 | Wilson et al. |
| 2020/0345408 A1 | 11/2020 | Orphanos et al. |
| 2021/0251515 A1 | 8/2021 | Korotko et al. |
| 2022/0160361 A1 | 5/2022 | Busch et al. |
| 2023/0065829 A1 | 3/2023 | Korotko |

FOREIGN PATENT DOCUMENTS

| | | |
|---|---|---|
| JP | 20180512933 | 5/2018 |
| JP | 20180171349 | 11/2018 |
| WO | 03013367 | 2/2003 |
| WO | 2017213491 | 12/2017 |

OTHER PUBLICATIONS

International Search Report for PCT/US2020/046188 dated Jan. 21, 2021, 9 pages.

English translation of Notice of Reasons for Rejection for JP Application No. 2022-508534, dated Apr. 9, 2024, 3 pages.

International Preliminary Report on Patentability for International Patent Application No. PCT/US2023/012724, filed Feb. 9, 2023, 6 pages.

* cited by examiner

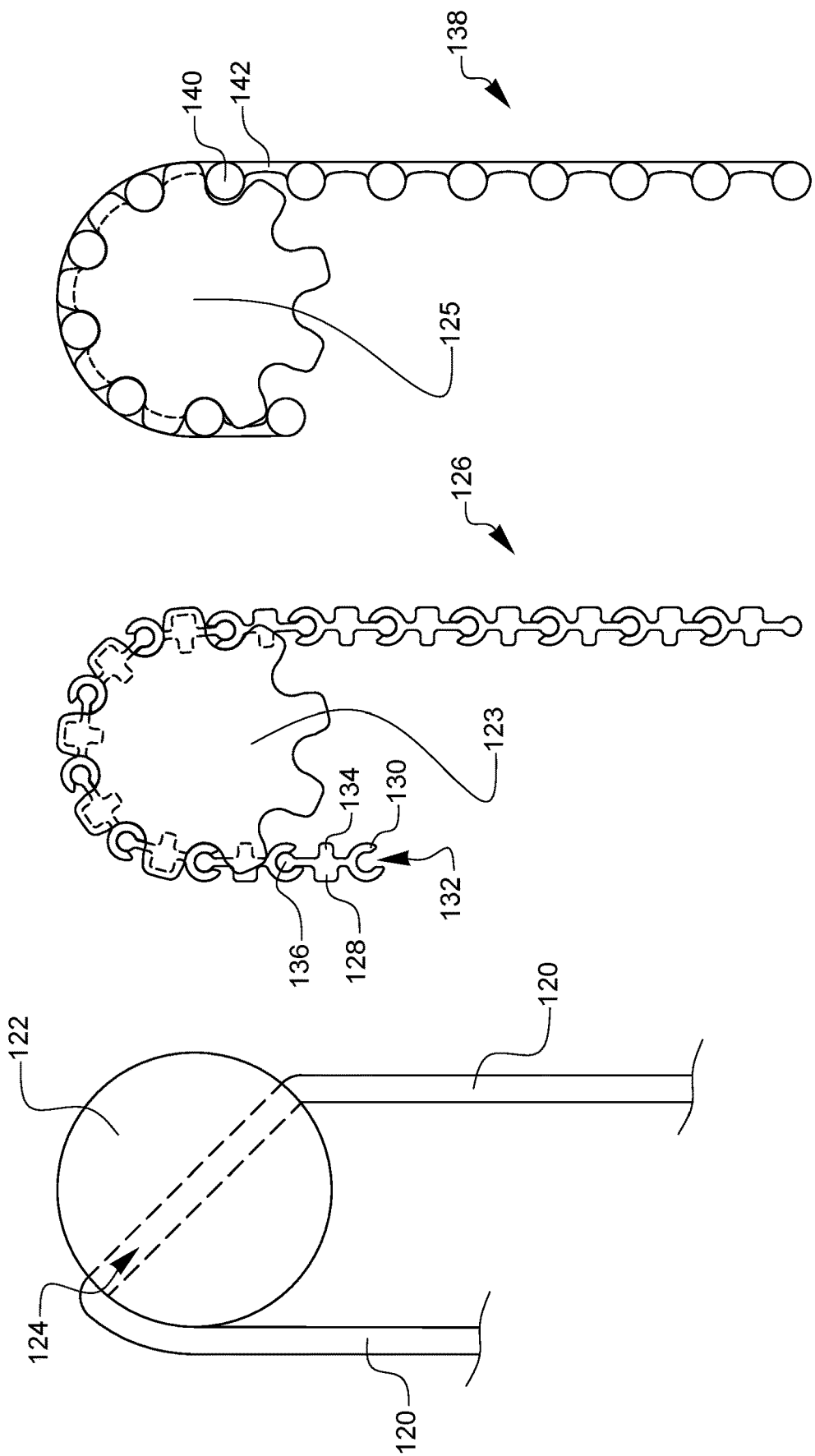

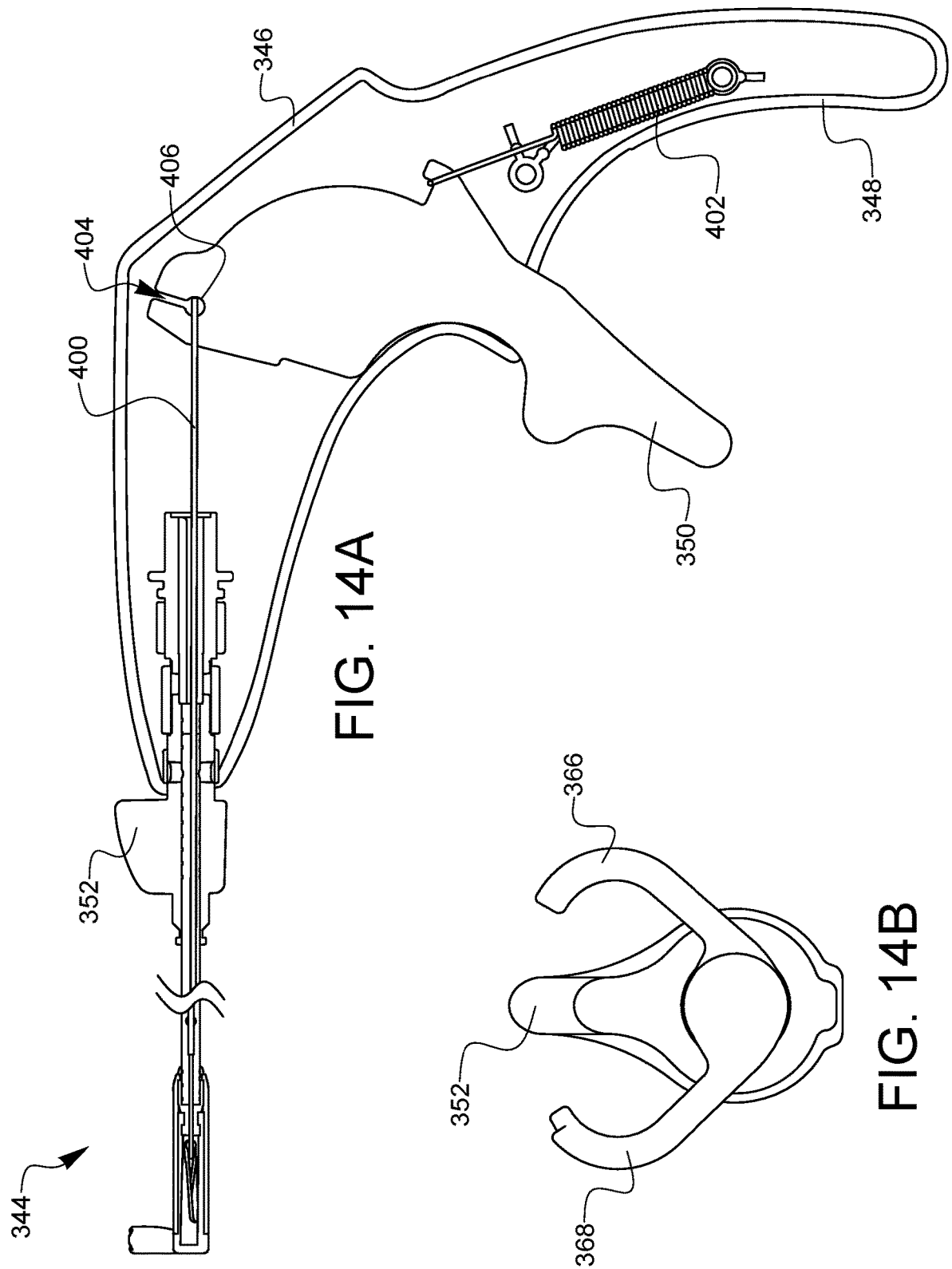

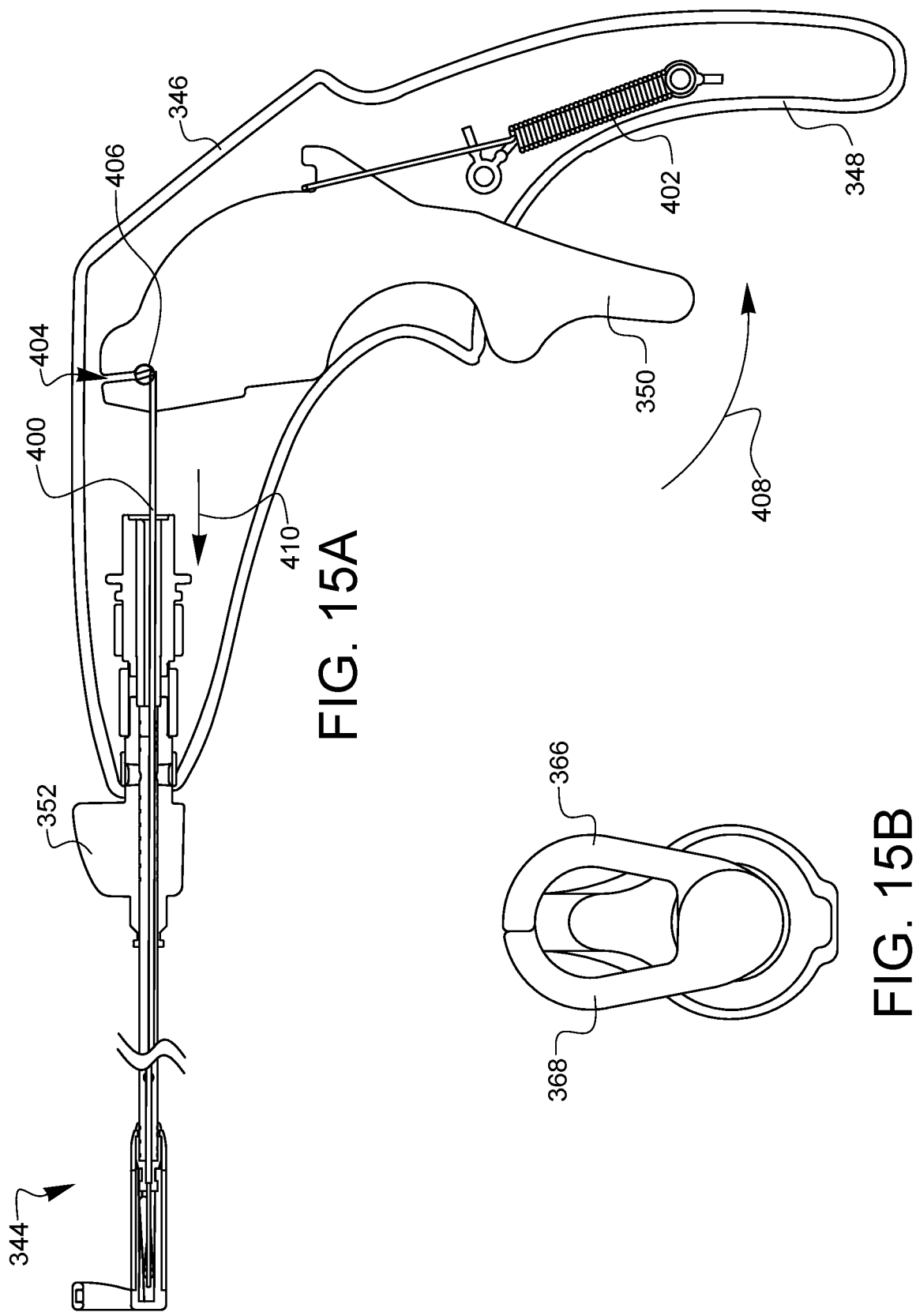

DEVICE FOR VESSEL HARVESTING

REFERENCE TO RELATED APPLICATIONS

This patent application claims priority to U.S. Provisional Patent Application No. 62/886,374 filed Aug. 14, 2019 and entitled "DEVICE FOR VESSEL HARVESTING." This patent application also claims priority to U.S. Provisional Patent Application No. 62/916,571 filed Oct. 17, 2019 and entitled "DEVICE FOR VESSEL HARVESTING." This patent application also claims priority to U.S. Provisional Patent Application No. 62/981,813 filed Feb. 26, 2020 entitled "DEVICE FOR VESSEL HARVESTING." The 62/886,374, 62/916,571, and 62/981,813 applications are hereby incorporated by reference in their entirety.

FIELD

The claimed invention relates to minimally invasive surgical devices, and more specifically to a surgical device used in vessel harvesting surgical procedures.

BACKGROUND

Minimally invasive surgical approaches are gaining increased interest in relation to coronary procedures. Coronary revascularization procedures such as the grafting of the internal thoracic artery (ITA) has shown superior long-term patency and improved patient outcome in coronary artery bypass graft (CABG) surgeries. While conventional approaches to ITA harvesting have included median sternotomy or multiple thoracoports, a minimally invasive approach is desirable. A minimally invasive procedure related to revascularization using either the left or right internal thoracic artery (ITA), or the left or right internal mammary artery (IMA) may utilize access to the ITAs via sub-xiphoid access, where increased surgical space is gained by accessing the internal thoracic arteries via incision at the subxiphocostal region.

Upon harvesting either the left internal thoracic artery (LITA) or the right internal thoracic artery (RITA) anastomoses to the left anterior descending (LAD) coronary artery and to the right coronary artery (RCA), respectively, can be performed without cardiopulmonary bypass (CPB). A significant advantage of this approach is that a perfectly harvested ITA graft can be perfectly anastomosed to the usual site on the LAD artery, or onto the RCA artery. A minimally invasive ITA harvesting procedure involving sub-xiphoid access also results in superior cosmetic results, is reasonably painless, and the arterial grafting can be accomplished on the beating heart. Recent approaches of minimally invasive ITA harvesting surgical techniques have been shown to result in increased effective length of ITA bypasses, reduced operation times, and improved patient recovery.

While less invasive surgical approaches for ITA harvesting and CABG have shown promise, the visualization, maintenance of insufflation, and distal suturing of a coronary anastomosis in totally endoscopic coronary artery bypass grafting on the beating heart is technically demanding. While minimally invasive surgical tools and procedures can create larger working spaces to accommodate additional surgical tools such as endoscopes, suturing tools, and the like. However, achieving an increased working space should ideally preserve chest wall integrity and avoid CPB. Likewise, a minimally invasive surgical approach should not compromise the reliability of a cardiac repair. Therefore, there is a need for suitable surgical tools to aid in the take-down or harvesting of ITA during minimally invasive harvesting and revascularization surgical procedures.

SUMMARY

A device for vessel harvesting is disclosed. The device for vessel harvesting may include a distal housing, a dissector coupled to the distal housing, a drive element coupled to the dissector, and an actuator coupled to the drive element.

Another device for vessel harvesting is disclosed, which may include a distal housing defining a rotatable dissector, a shaft coupled to the distal housing may further include a first articulation joint movable within a first plane, and a second articulation joint movable within a second plane, which is substantially perpendicular to the first plane, a barrel chain drive element coupled to the rotatable dissector, and an actuator coupled to the drive element.

Another device for vessel harvesting is disclosed. The device for vessel harvesting may include a shaft and a dissector coupled to the shaft.

Another device for vessel harvesting is disclosed. The device for vessel harvesting may include a shaft, a distal tip defining an arcuate finger coupled to a distal end of the shaft, and a member slidably engaged to the distal tip.

BRIEF DESCRIPTION OF THE DRAWINGS

FIGS. 4A-4C are partial cross-sectional top views of alternate embodiments of drive mechanisms for a minimally invasive surgical device.

FIGS. 14A and 14B are a side cross-sectional view and front end view, respectively, of the minimally invasive surgical device of FIG. 11 in an open position.

FIGS. 15A and 15B are a side cross-sectional view and front end view, respectively, of the minimally invasive surgical device of FIG. 11 in a closed position.

Figure 1:
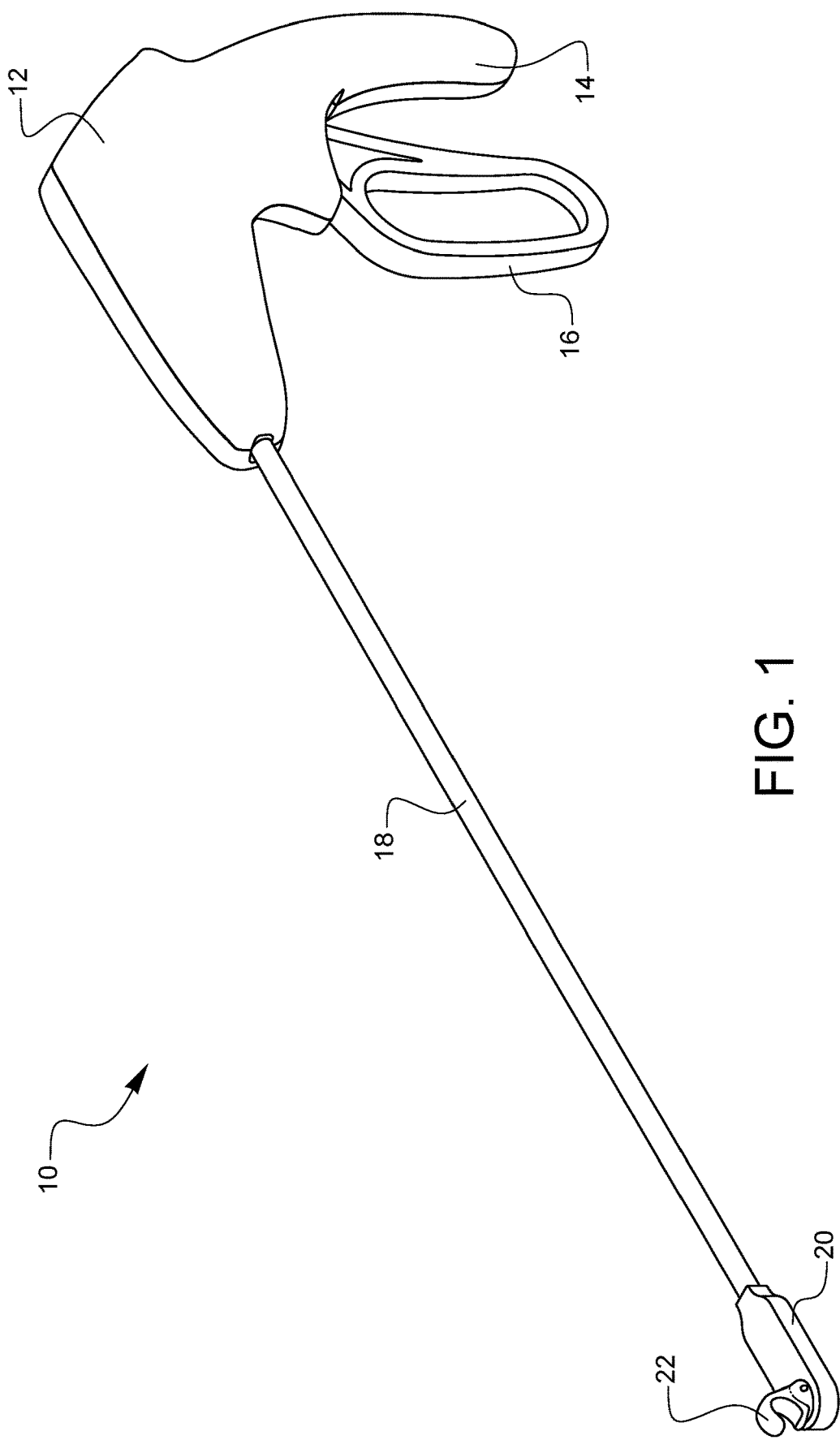
FIG. 1 is a top-left-front perspective view of one embodiment of a minimally invasive surgical device.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1 is a top-left-front perspective view of one embodiment of a minimally invasive vessel harvesting device 10. The minimally invasive vessel harvesting device 10 has a housing 12 which extends down to form a handle 14. The device also has an actuation lever 16 pivotably coupled to the handle 14. The minimally invasive vessel harvesting device 10 also has a shaft 18 which is coupled to the housing 12. The minimally invasive vessel harvesting device 10 has a distal tip housing 20 on the opposite end of the shaft 18 which defines a blunt dissector 22 used in a minimally invasive surgical procedure involving the harvesting of IMA for revascularization. The blunt dissector 22 is coupled to the actuation lever 16, and movement of the actuation lever 16 will rotate the blunt dissector 22 to achieve adjustable positioning of the blunt dissector 22 during use in a minimally invasive cardiovascular procedure such as the harvesting of internal thoracic arteries. This mechanism will be described in further detail. The blunt dissector 22 is an arcuate or curved appendage that has a smooth, atraumatic tip allowing for and enabling the gentle manipulation and separation of tissue, while preventing damage to anatomical features and structures surrounding the tissue of interest. Blunt dissection, in general, refers to an element of surgical procedure where careful separation of tissues is accomplished with the use of fingers or blunt surgical tools. The blunt dissector tip is useful in procedures related to ITA/IMA take-down or harvesting procedures. The shape, maneuverability, and atraumatic nature of the blunt dissector 22 are features that contribute to improved utility, reduced risk of harming surrounding tissue, and achieving positive results during a minimally invasive surgical procedure. While the blunt dissector 22 shown in FIG. 1 is an atraumatic, arcuate appendage, or gentle finger, other embodiments may be blunt, partially blunt, or have partial edges. Still other embodiments may have portions or edges that may be partially sharpened or shaped as needed for their intended surgical procedure. While an actuation lever is shown in this embodiment, other embodiments may include an actuator such as a lever, sliding rod, knob, pulley, gear, solenoid, motor, or other actuator known to those skilled in the art.

Figure 2A:
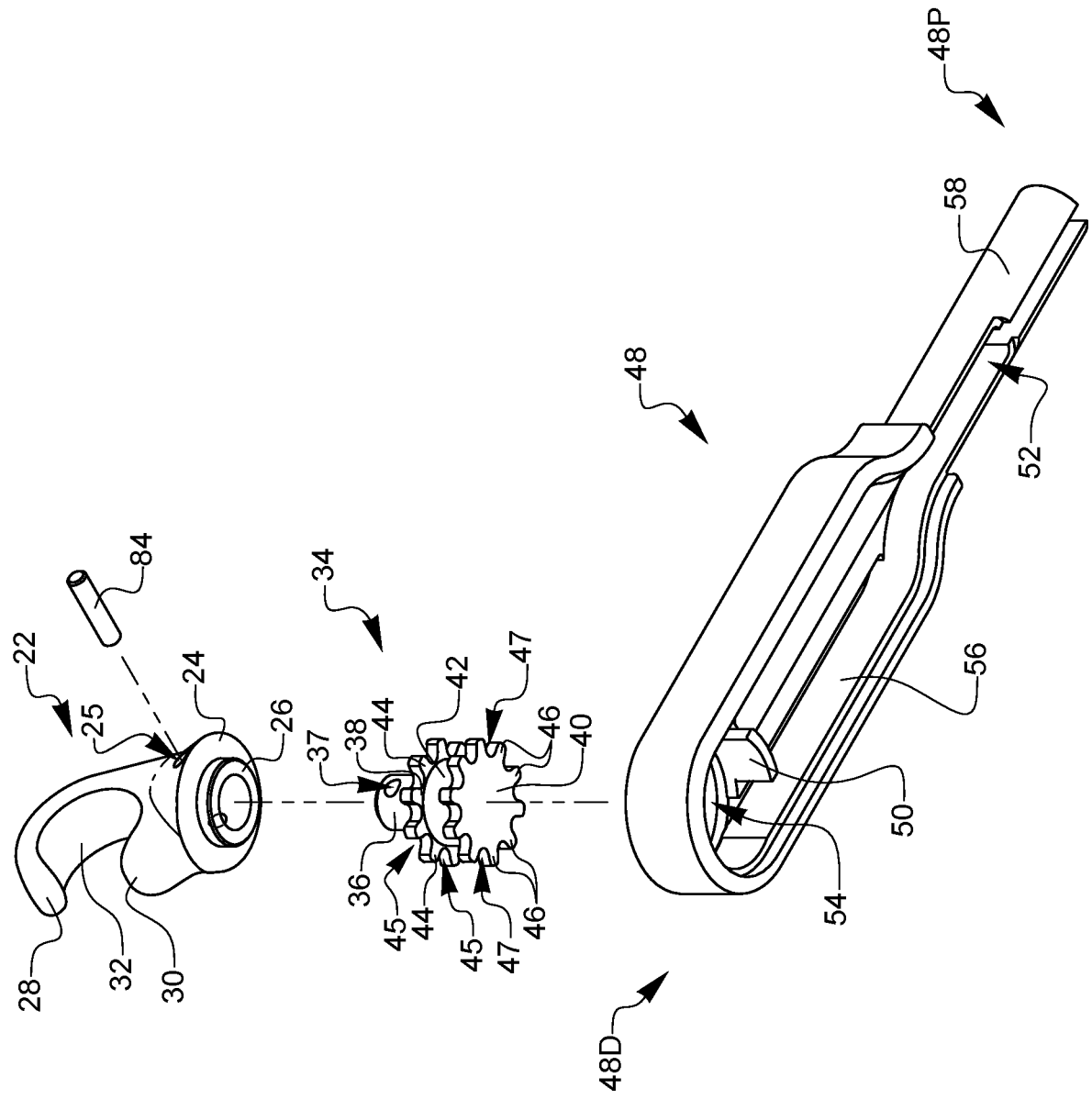
FIGS. 2A-2C are a series of exploded views illustrating the assembly steps of the minimally invasive surgical device of FIG. 1.
Figure 2B:
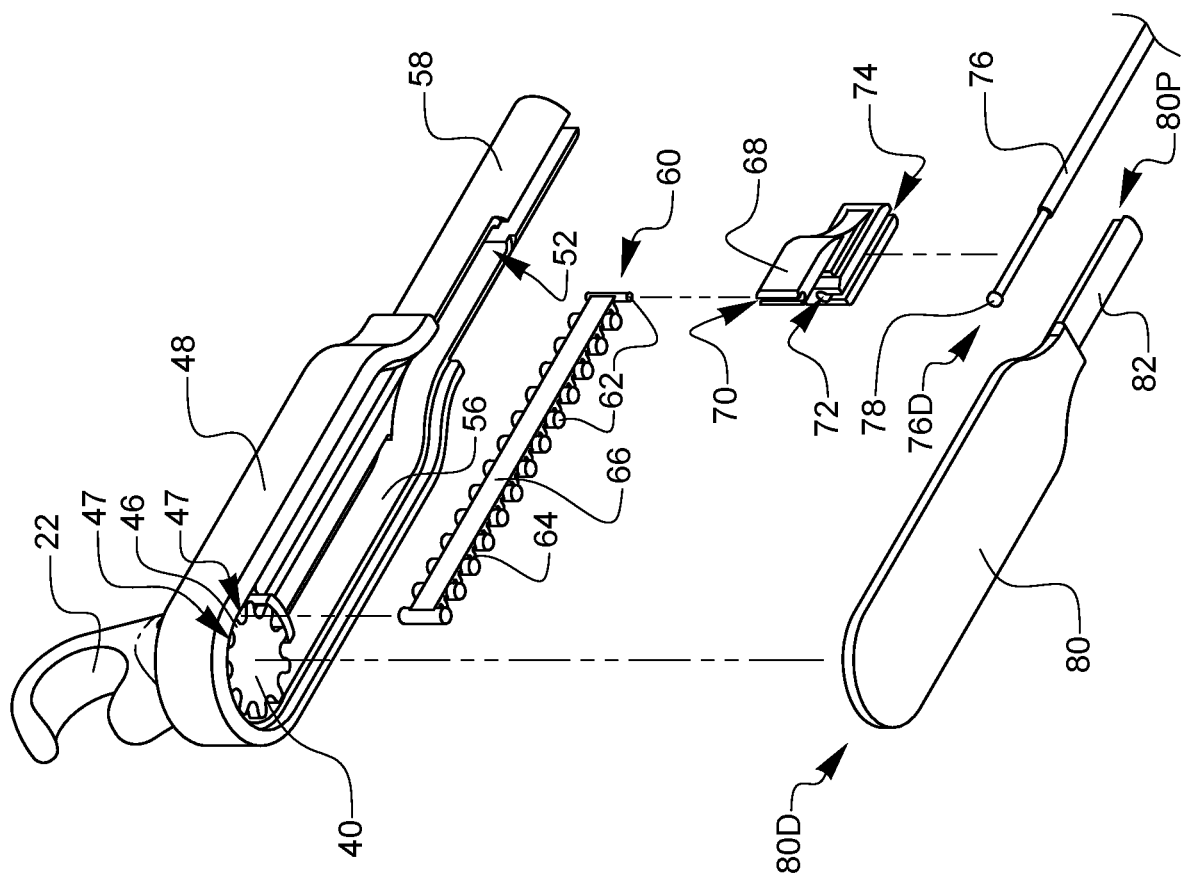
Figure 2C:
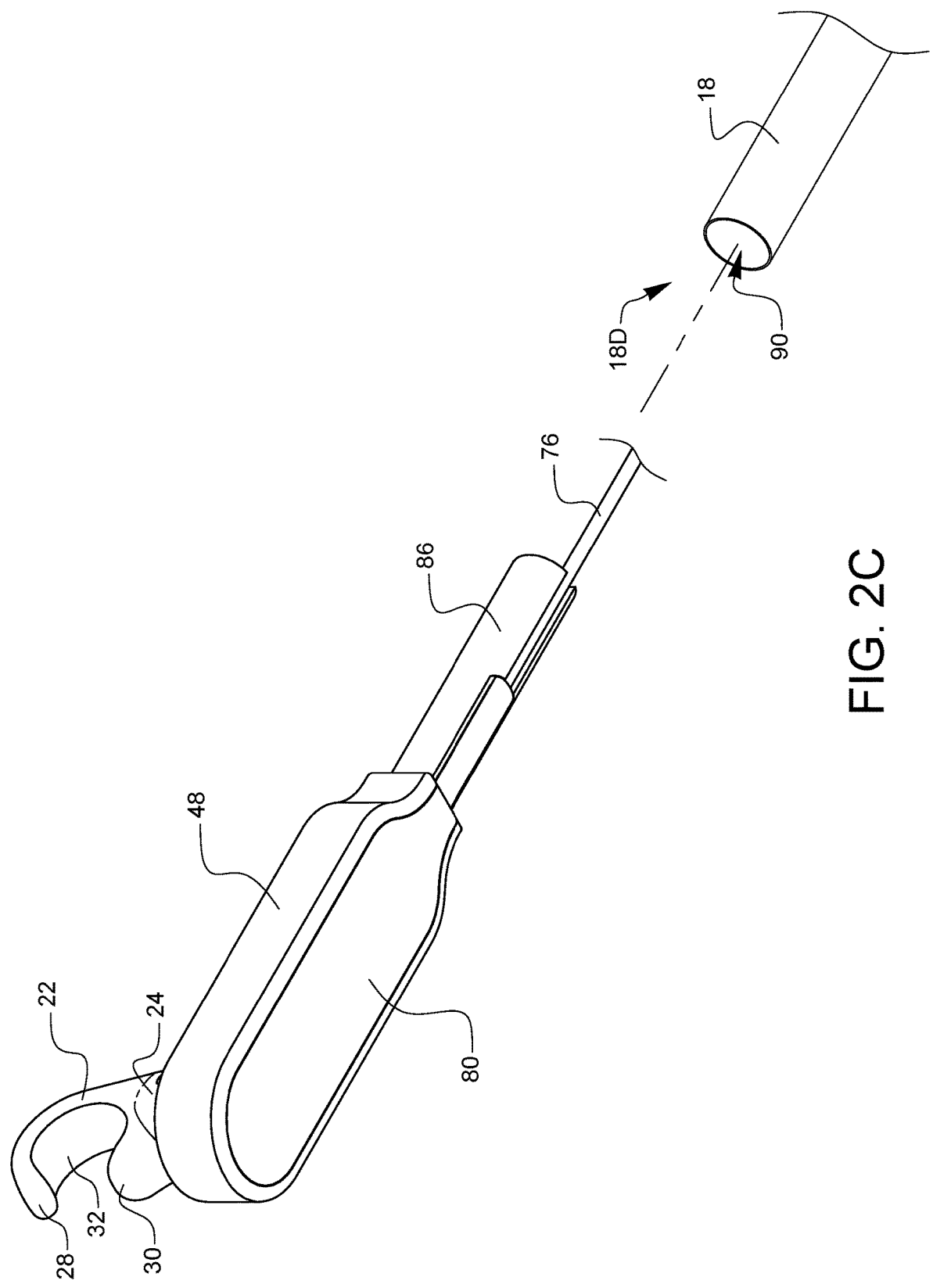

FIGS. 2A-2C are a series of exploded views illustrating the assembly steps of the minimally invasive surgical device of FIG. 1. FIG. 2A illustrates the assembly steps of the distal tip housing 20 of the minimally invasive vessel harvesting device 10. A blunt dissector 22 defining an upper dissector 28, lower dissector 30, and having an inner surface 32 also defines a dissector base 24 and a hub 26. A gear assembly 34 defining a gear shaft 36 having an upper gear 38, lower gear 40 and capstan 42 is placed inside the inner diameter of the hub 26 on the blunt dissector 22. The upper gear 38 has several teeth 44 and recesses 45 interposed between the teeth 44. Likewise, the gear 40 also has several teeth 46 and recesses 47 interposed between the teeth 46. A pin 84 is inserted into hole 25 on the blunt dissector 22 and into a corresponding hole 37 on the gear assembly 34. While a pin is used to assemble these components, other means of assembly may also be used, such as adhesion, welding, or utilizing a single component in another embodiment that defines the dissector and the gear assembly. Next, the blunt dissector 22 and gear assembly 34 are placed into a hole 54 on a distal end 48D of an upper distal tip housing 48. The upper distal tip housing 48 also defines an alignment guide 50, a side wall 56, and a tube portion 58 at a proximal end 48P. The tube portion 58 further defines an internal channel 52.

FIG. 2B illustrates the continued assembly of the minimally invasive vessel harvesting device 10 of FIG. 1. A drive element, in this embodiment a barrel chain 60, having several barrel 62 portions interposed between several tab 64 portions along a wall 66 of the barrel chain 60 is placed inside the upper distal tip housing 48 such that the wall 66 of the barrel chain 60 rides against the side wall of the upper distal tip housing 48 opposite side wall 56, the barrels 62 are captured in the recesses 47 between the teeth 46 on the lower gear 40 and also in the recesses 45 between the teeth 44 on the upper gear 38 (although not visible in this view), around the gear assembly and against the side wall 56 of the upper distal tip housing 48. It should be noted that the tabs 64 are sized and configured such that they will provide stiffness to the barrel chain 60 as well as maintain alignment and tracking of the barrel chain 60 in the capstan 42 portion, not visible here, of the gear assembly 34. A drive coupler 68 having a drive element coupler 70 and a drive rod coupler 72 at the end of a drive rod slot 74 is coupled to the end of the barrel chain 60 by fitting the drive element coupler 70 of the drive coupler 68 over the terminating barrel 62 in the barrel chain 60. A drive rod 76 having a ball end 78 at the distal end 76D of the drive rod 76 is captured in the drive rod coupler 72 by placing the ball end 78 into the drive rod coupler 72 and guiding the drive rod 76 through the drive rod slot 74 on the drive coupler 68. The drive rod 76 and the drive coupler 68 are freely movable within the channel 52 inside the tube portion 58 of the upper distal tip housing 48. A lower distal tip housing 80 having a tube portion 82 at a proximal end 80P is fixedly attached to the upper distal tip housing 48, completing the assembly of the upper distal tip housing 48. FIG. 2C illustrates another assembly step in the minimally invasive vessel harvesting device 10. The distal tip housing tube 86 with the drive rod 76 protruding is inserted into a shaft opening 90 of a distal end 18D of the shaft 18 on the minimally invasive vessel harvesting device 10. This distal tip housing tube 86 is fixedly attached to the shaft 18 by welding, brazing or other methods known to those skilled in the art. Further assembly steps of the device including the handle, lever and other components is well known to those skilled in the arts of minimally invasive vessel harvesting devices. It should be noted that while a barrel chain drive is described in regard to the embodiment described herein, that other drive elements or drive mechanisms may also be used in other embodiments of the minimally invasive vessel harvesting device. The embodiment shown has a monolithic, or single piece barrel chain as the drive element. A drive element could include a chain or a belt, a coupler, a drive rod or a combination thereof. Alternate drive attachments to the gear assembly including the capstan and gears shown herein may be used, for example, slotted shafts or spools, cylindrical bearings or bushings, or other rotatable shafts known to those skilled in the art. Any structural element suitable for extending from or attaching to the blunt dissector for the purpose of attaching a drive element to and rotating the blunt dissector would be a suitable drive attachment. Alternative drive elements to the barrel chain and drive coupler may also be used as drive elements in other embodiments of the minimally invasive vessel harvesting device described herein. Stiff belts, rods, wires, linked chains, or other linkages known in the art capable of pushing or pulling on a drive attachment coupled to a blunt dissector may be used as drive elements in alternate embodiments.

Figure 3A:
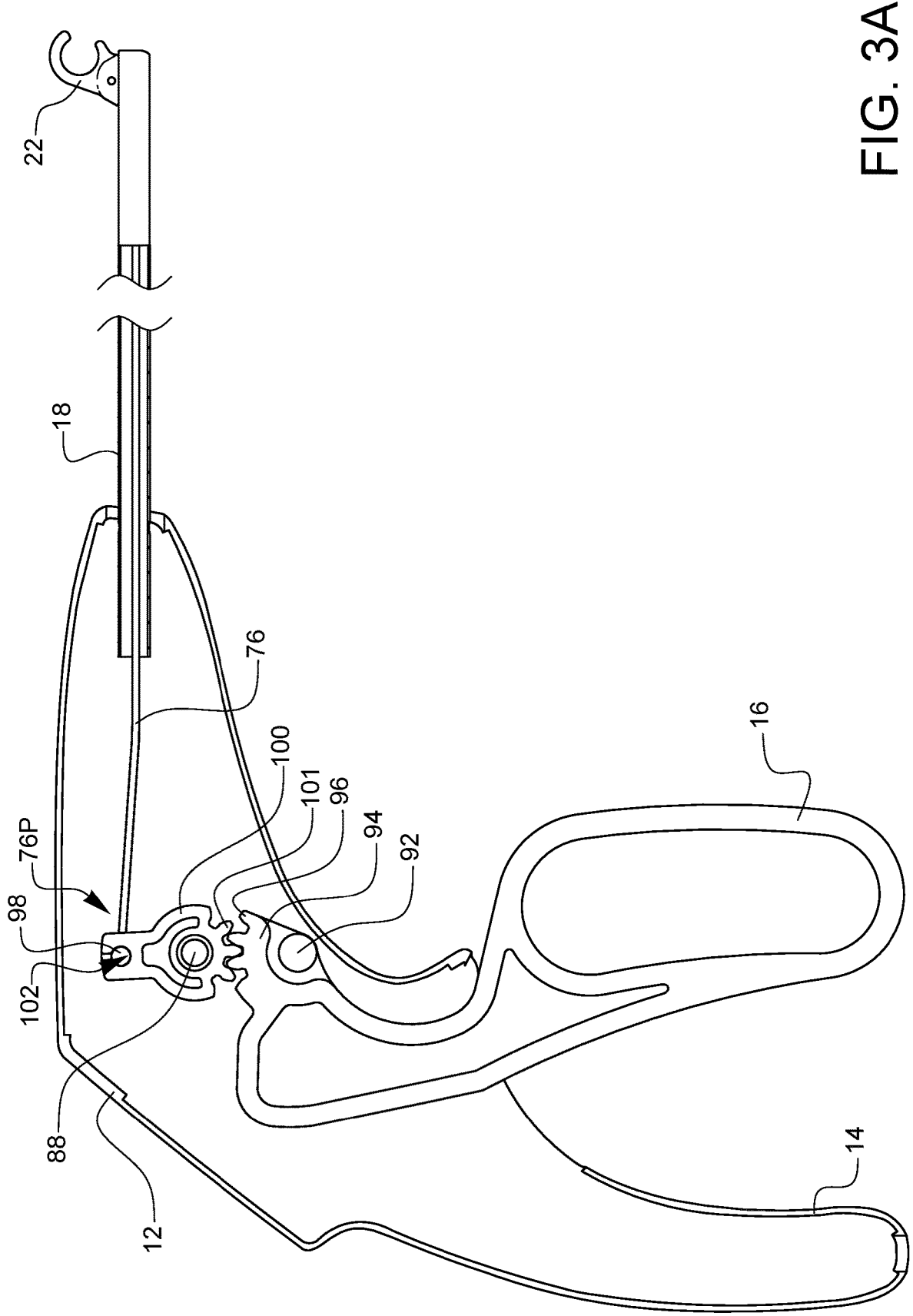
FIGS. 3A and 3B are side cross-sectional and top cross-sectional views, respectively, of the minimally invasive surgical device of FIG. 1, illustrating the operational principles of the minimally invasive surgical device.
Figure 3B:
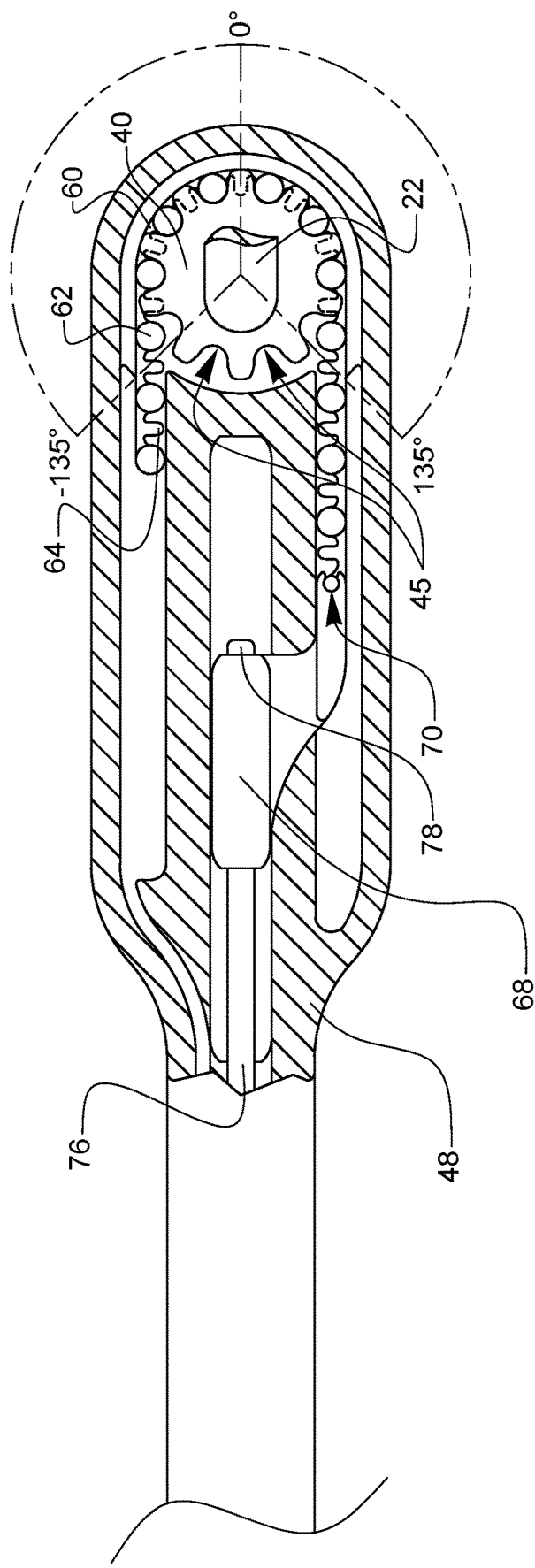

FIGS. 3A and 3B are side cross-sectional and top cross-sectional views, respectively, of the minimally invasive vessel harvesting device of FIG. 1, illustrating the operational principles of the minimally invasive vessel harvesting device. FIG. 3A illustrates the invasive vessel harvesting device 10 in a neutral position with respect to the position of the actuation lever 16 and the blunt dissector 22. The actuation lever 16 is in a position partially away from the handle 14, and the blunt dissector 22 is oriented in a position such that it is aligned with the shaft 18 of the minimally invasive vessel harvesting device 10. The internal components of the actuation lever 16 are also visible in the cross-sectional view of FIG. 3A. The actuation lever 16 is pivotably coupled about a pivot 92 and also defines a lever gear 94 with several lever gear teeth 96. A drive gear 100 pivots about a pivot point 88, and the drive gear 100 defines several teeth 101 and a drive gear coupler 102. The teeth 101 on the drive gear 100 engage with the teeth 96 on the lever gear 94. The drive rod 76 has a drive rod coupling ball 98 on its proximal end 76P, which is held within the drive gear coupler 102.

FIG. 3B is a top cross-sectional view of the upper distal tip housing 48, illustrating the position of the components within the upper distal tip housing 48, particularly the blunt dissector 22 corresponding to the lever position shown in FIG. 3A. It should be noted that in this position shown in FIG. 3B, the blunt dissector 22 is oriented in such a fashion that the arcuate portion of the blunt dissector 22 is aligned with the shaft 18 of the minimally invasive vessel harvesting device 10, at an angle of approximately 0 degrees in reference to the angle indicator shown in FIG. 3B.

Figure 3C:
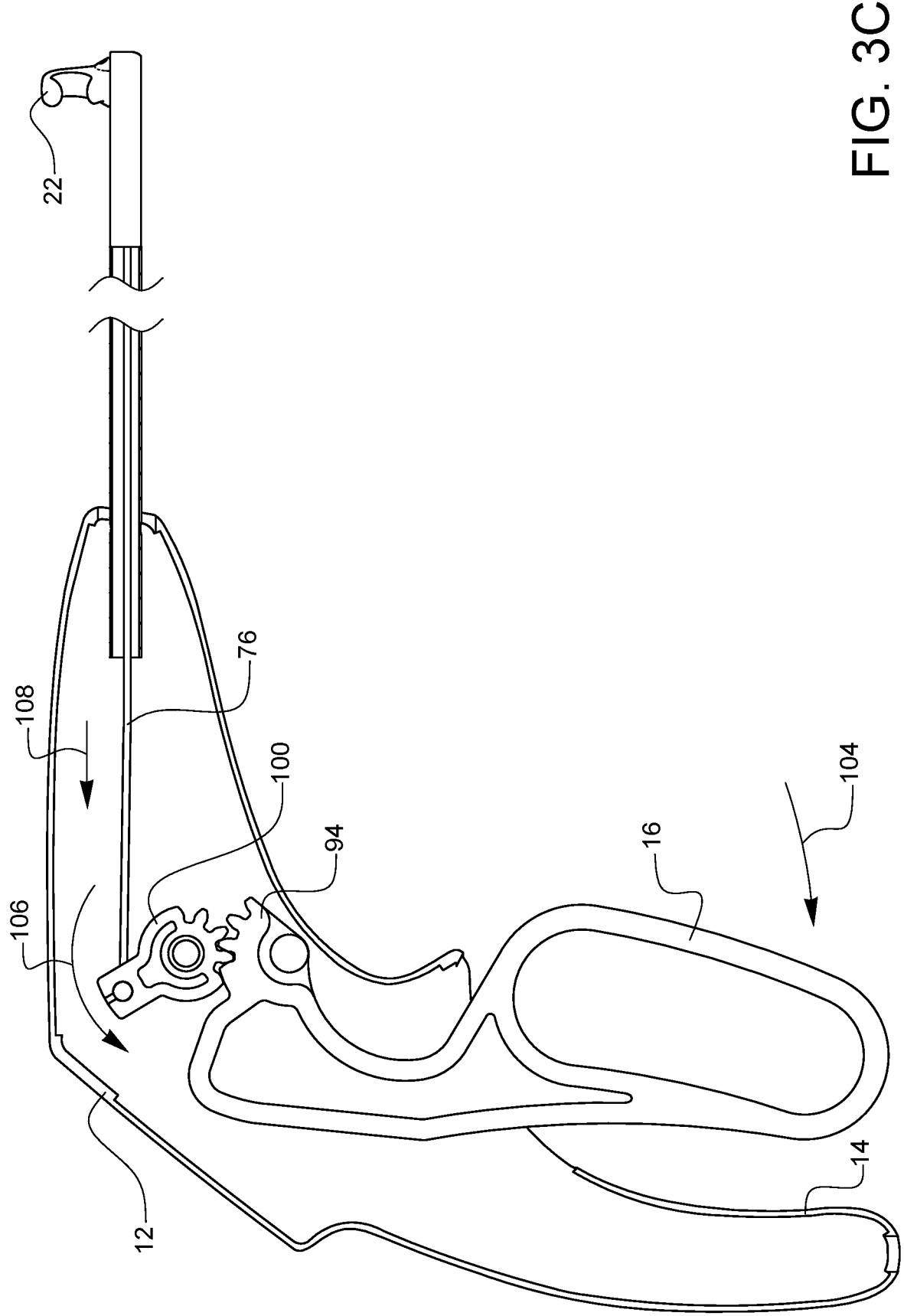
FIGS. 3C and 3D are side cross-sectional and top cross-sectional views, respectively, of the minimally invasive surgical device of FIG. 1, illustrating the operational principles of the minimally invasive surgical device.
Figure 3D:
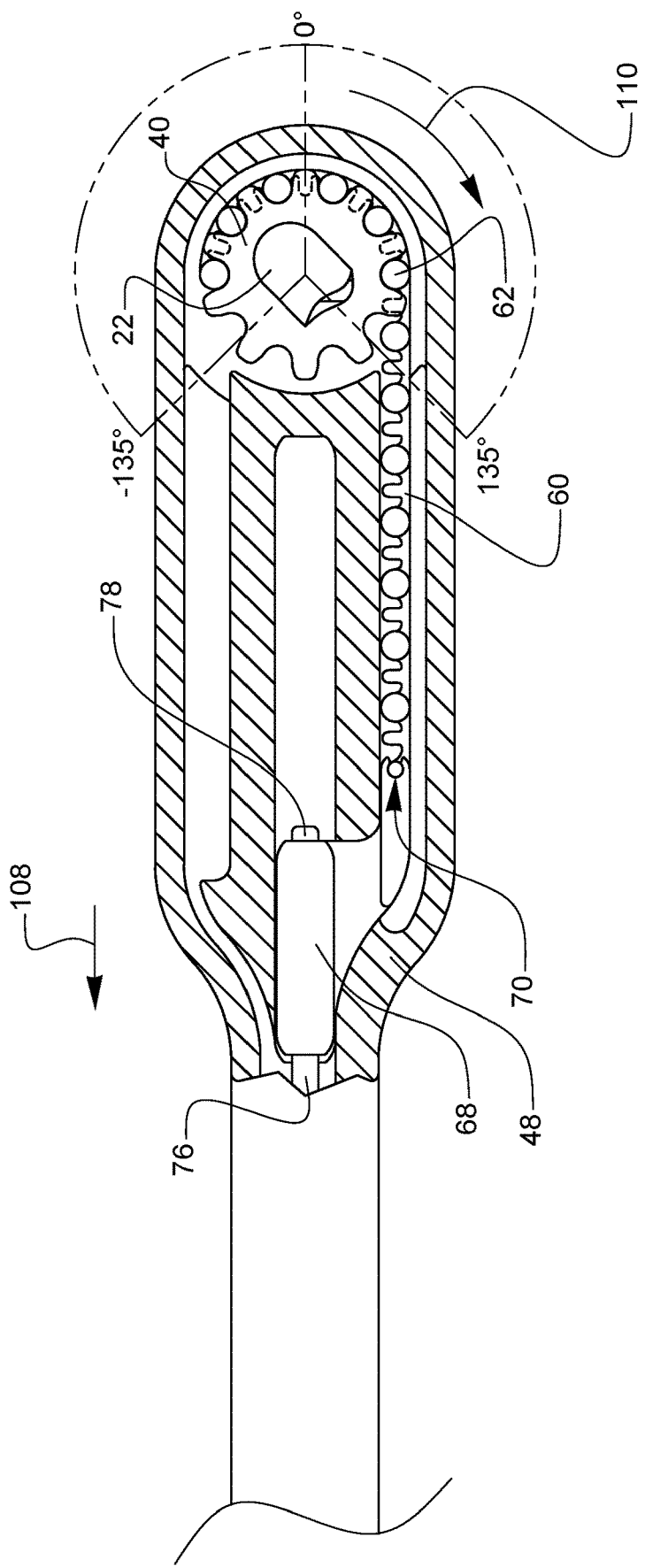

FIGS. 3C and 3D are side cross-sectional and top cross-sectional views, respectively, of the minimally invasive vessel harvesting device of FIG. 1, illustrating the operational principles of the minimally invasive vessel harvesting device. FIG. 3C illustrates the invasive vessel harvesting device 10 in a rotated position with respect to the position of the actuation lever 16 and the blunt dissector 22. The actuation lever 16 is in a position squeezed in a direction 104 towards the handle 14, and the blunt dissector 22 is oriented in a position such that it is rotated clockwise in reference to the shaft 18 of the minimally invasive vessel harvesting device 10. When the lever 16 is squeezed towards the handle 14, the lever gear 94 engages lever drive gear 100 and rotates the lever drive gear 100 in direction 106. Since the lever drive gear 100 is coupled to the drive rod 76, the drive rod 76 is pulled in direction 108. FIG. 3D is a top cross-sectional view of the upper distal tip housing 48, illustrating the position of the components within the upper distal tip housing 48, particularly the blunt dissector 22 corresponding to the lever position shown in FIG. 3C. As drive rod 76 is pulled in direction 108, drive coupler 68 is also pulled in direction 108 as the ball end 78 of the drive rod 76 is coupled to the drive coupler 68. The barrel chain 60 is also pulled in direction 108, as the barrel chain 60 coupled to the drive element coupler 70 on the drive coupler 68. Thus, the blunt dissector 22 is rotated in direction 110 as the barrel chain 60 engages with the teeth 46 on lower gear 40, being at an angle of approximately 135 degrees in reference to the angle indicator shown in FIG. 3D.

Figure 3E:
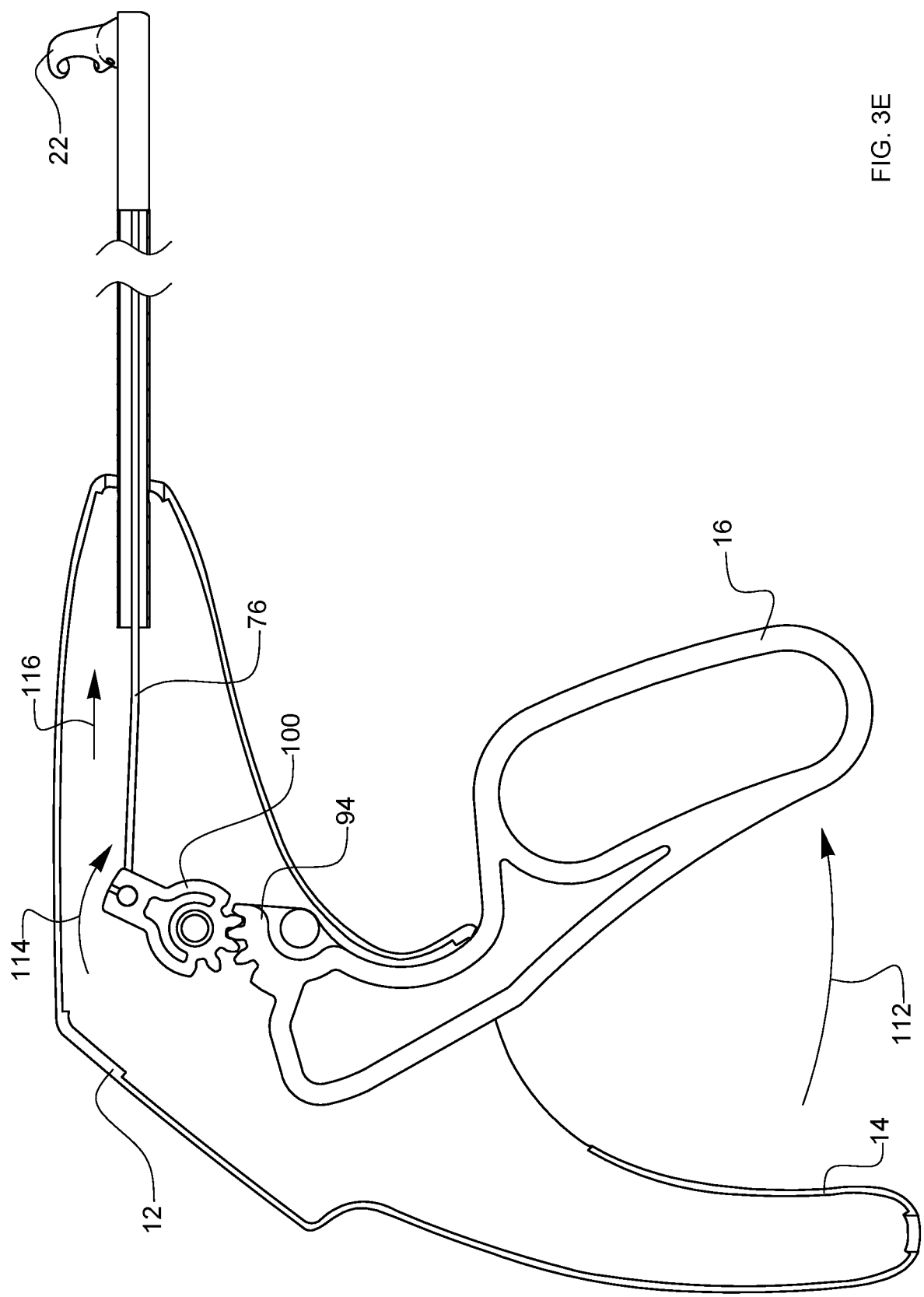
FIGS. 3E and 3F are side cross-sectional and top cross-sectional views, respectively, of the minimally invasive surgical device of FIG. 1, illustrating the operational principles of the minimally invasive surgical device.
Figure 3F:
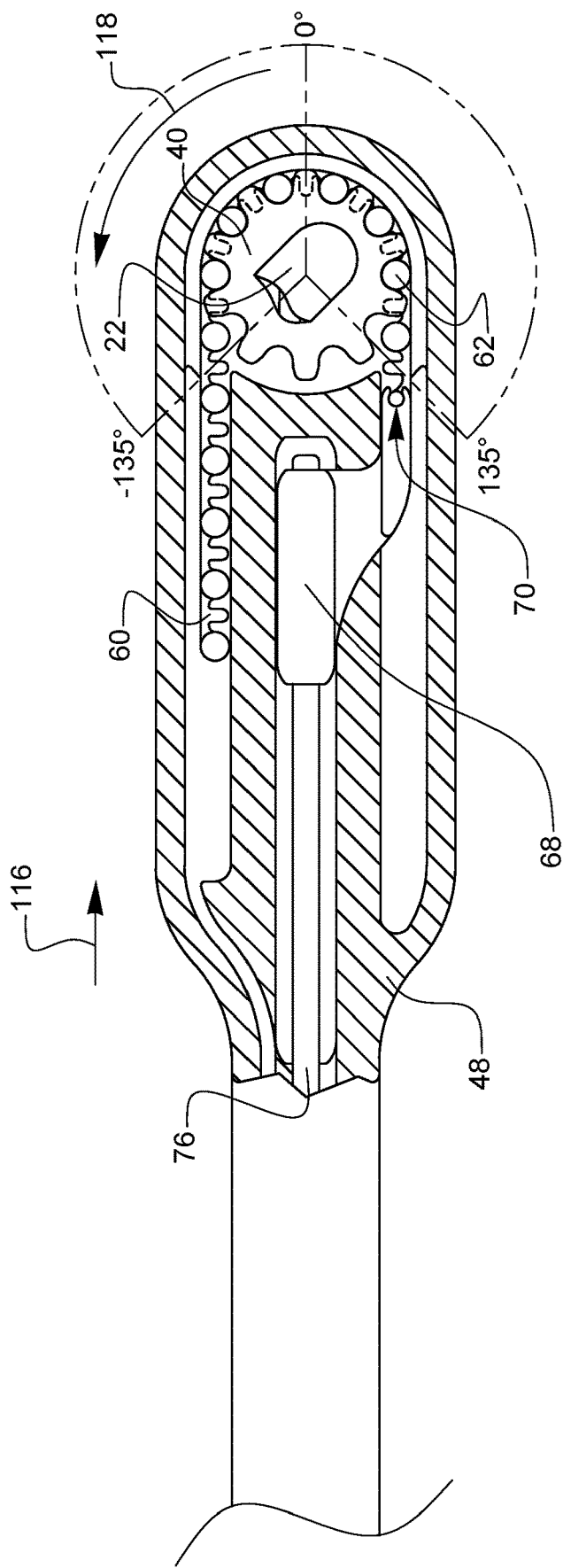

FIGS. 3E and 3F are side cross-sectional and top cross-sectional views, respectively, of the minimally invasive vessel harvesting device of FIG. 1, illustrating the operational principles of the minimally invasive vessel harvesting device. FIG. 3E illustrates the invasive vessel harvesting device 10 in another rotated position with respect to the position of the actuation lever 16 and the blunt dissector 22. The actuation lever 16 is in an open moved in a direction 112 away from the handle 14, and the blunt dissector 22 is oriented in a position such that it is rotated counterclockwise in reference to the shaft 18 of the minimally invasive vessel harvesting device 10. When the lever 16 is moved away from the handle 14, the lever gear 94 engages lever drive gear 100 and rotates the lever drive gear 100 in direction 114. Since the lever drive gear 100 is coupled to the drive rod 76, the drive rod 76 is pushed in direction 116. FIG. 3F is a top cross-sectional view of the upper distal tip housing 48, illustrating the position of the components within the upper distal tip housing 48, particularly the blunt dissector 22 corresponding to the lever position shown in FIG. 3E. As drive rod 76 is pushed in direction 116, drive coupler 68 is also pushed in direction 116 as the ball end 78 of the drive rod 76 is coupled to the drive coupler 68. The barrel chain 60 is also pushed in direction 116, as the barrel chain 60 coupled to the drive element coupler 70 on the drive coupler 68. The tabs 64 on the barrel chain 60, as previously described, provide additional support and stiffness to the barrel chain 60 and allow the chain to be pushed. Thus, the blunt dissector 22 is rotated in direction 118 as the barrel chain 60 engages with the teeth 46 on lower gear 40, at an angle of approximately −135 degrees in reference to the overlaid angle indicator shown in FIG. 3F. The embodiment described herein has a blunt dissector 22 which is pivotable relative to the distal housing and is pivotable in a rotation range of about 270 degrees in reference to the overlaid angle indicator shown in FIGS. 3B, 3D, and 3F. This rotation of the blunt dissector 22 is pivotable about a plane that is substantially parallel to the distal housing. Other embodiments including a rotatable dissector such as the one described herein may be configured to rotate over a full range of about 210 degrees, about 270 degrees or about 360 degrees. The rotation range of the blunt dissector 22 enables a precise control over the articulation and position of the blunt dissector during surgical procedures involving vessel harvesting.

FIGS. 4A-4C are partial cross-sectional top views of alternate embodiments of drive mechanisms for a minimally invasive vessel harvesting device. FIG. 4A is a partial cross-sectional top view of a belt drive element 120 which is coupled to a drive shaft 122 similar to the capstan of the embodiment of a vessel harvesting device as shown in FIGS. 1-3F. This drive shaft 122 has a capstan slot 124 into which the belt drive element 120 is fixedly attached.

FIG. 4B is a partial cross-sectional top view of a segmented chain drive 126 which is coupled to a gear assembly drive shaft 123 similar to the capstan of the embodiment of a vessel harvesting device as shown in FIGS. 1-3F. This segmented chain drive 126 has a gear assembly drive shaft 123 around which the segmented chain drive 126 is coupled. The segmented chain drive 126 is made of several links 128. Each link 128 defines a clasp 13 having a recess 132, a support tab 134, and a peg 136. Each link 128 is connected to another subsequent link 128 by connecting a tab 136 one link 128 to a recess 132 on the subsequent link 128.

FIG. 4C is a partial cross-sectional top view of another embodiment of a barrel chain 138 comprised of a single piece having several barrels 140 disposed upon a chain wall 142 and spaced such that they engage with and couple to with the gears on a gear assembly drive shaft 125, similar to the capstan of the embodiment of a vessel harvesting device as shown in FIGS. 1-3F.

Figure 5A:
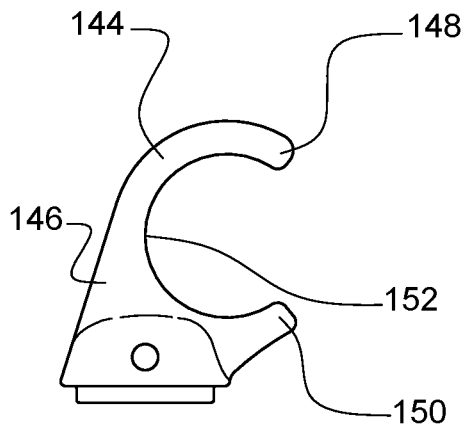
FIGS. 5A-5H are side views of alternate embodiments of dissectors for a minimally invasive surgical device.
Figure 5B:
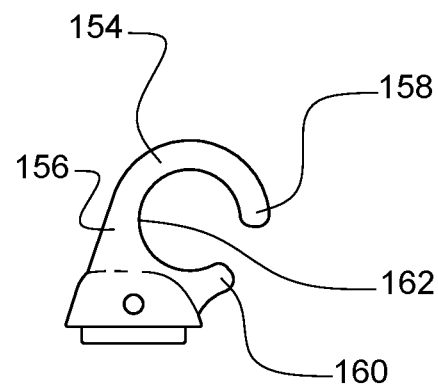
Figure 5C:
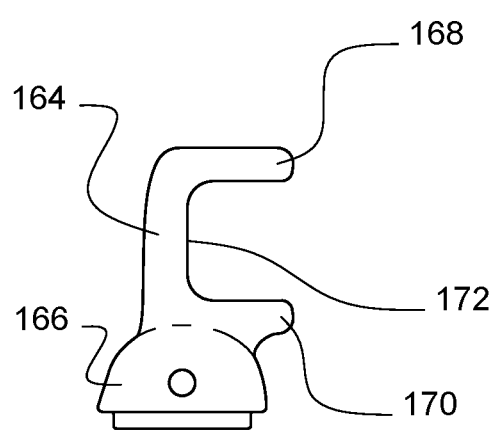
Figure 5D:
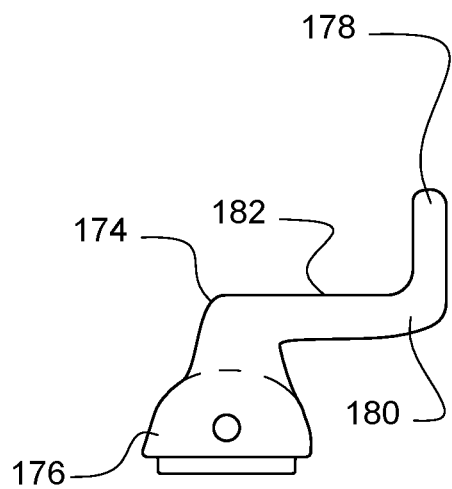
Figure 5E:
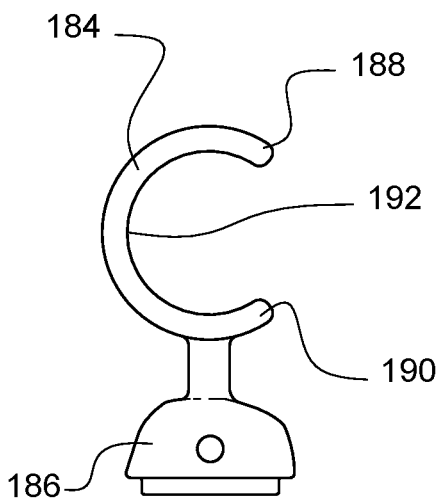
Figure 5F:
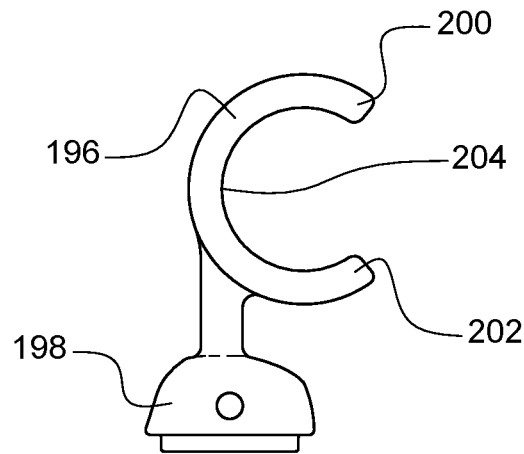
Figure 5G:
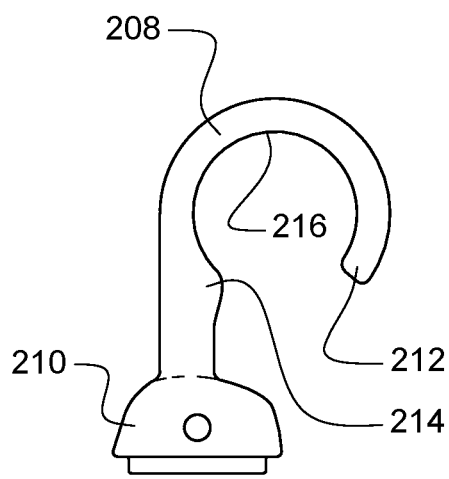
Figure 5H:
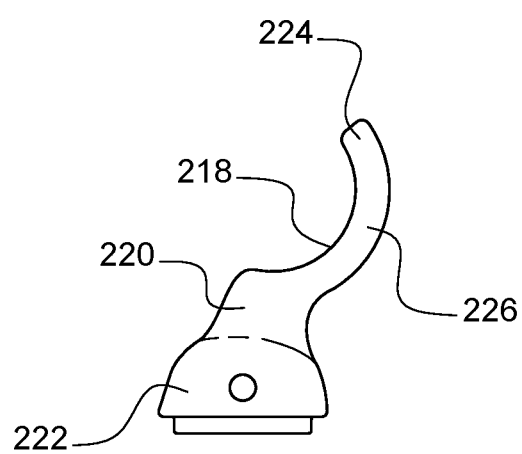

FIGS. 5A-5H are side views of alternate embodiments of dissectors for a minimally invasive vessel harvesting device. FIG. 5A is a side view of an alternate embodiment of a dissector for a minimally invasive vessel harvesting device. FIG. 5A shows a dissector 144 having a dissector base 146, an upper dissector 148, and a lower dissector 150. The dissector 144 also defines an inner surface 152. This dissector 144 has an arcuate, C-shaped profile with an opening on one side. FIG. 5B is a side view of an alternate embodiment of a dissector for a minimally invasive vessel harvesting device. FIG. 5B shows a dissector 154 having a dissector base 156, an upper dissector 158, and a lower dissector 160. The dissector 144 also defines an inner surface 152. This dissector 144 has an arcuate, C-shaped profile with an opening facing a slightly downward angle. FIG. 5C is a side view of an alternate embodiment of a dissector for a minimally invasive vessel harvesting device. FIG. 5C shows a dissector 164 having a dissector base 166, an upper dissector 168, and a lower dissector 170. The dissector 164 also defines an inner surface 172. This dissector 164 has an angular square-like profile with a side facing opening. FIG. 5D is a side view of an alternate embodiment of a dissector for a minimally invasive vessel harvesting device. FIG. 5D shows a dissector 174 having a dissector base 176, an upper dissector 178, a lower dissector 180. The dissector 174 also defines an inner surface 182. This dissector 174 has an angular, L-shaped profile. FIG. 5E is a side view of an alternate embodiment of a dissector for a minimally invasive vessel harvesting device. FIG. 5E shows a dissector 184 having a dissector base 186, an upper dissector 188, a lower dissector 190. The dissector 184 also defines an inner surface 192. This dissector 184 has an arcuate, C-shaped profile with a side facing opening. FIG. 5F is a side view of an alternate embodiment of a dissector for a minimally invasive vessel harvesting device. FIG. 5F shows a dissector 196 having a dissector base 198, an upper dissector 200, a lower dissector 202. The dissector 196 also defines an inner surface 204. This dissector 196 has an arcuate, C-shaped profile with a side facing opening. FIG. 5G is a side view of an alternate embodiment of a dissector for a minimally invasive vessel harvesting device. FIG. 5G shows a dissector 208 having a dissector base 210, an upper dissector 212, a lower dissector 214. The dissector 208 also defines an inner surface 216. This dissector 208 has an arcuate, C-shaped profile with a downward facing opening. FIG. 5H is a side view of an alternate embodiment of a dissector for a minimally invasive vessel harvesting device. FIG. 5H shows a dissector 226 having a dissector base 222, an upper dissector 224, a lower dissector 220. The dissector 224 also defines an inner surface 218. This dissector 224 has an arcuate, half C-shaped profile. Alternate embodiments of dissectors may have shapes such as L-shaped, corkscrew, or have sharper angles than embodiments directly illustrate herein. The inner surface of some of the alternate embodiments of the dissectors described herein may have smooth, textured, or conformable surfaces. Alternate embodiments of dissectors may be composed of materials such as plastic, metal, ceramic, composites, or combinations thereof.

Figure 6:
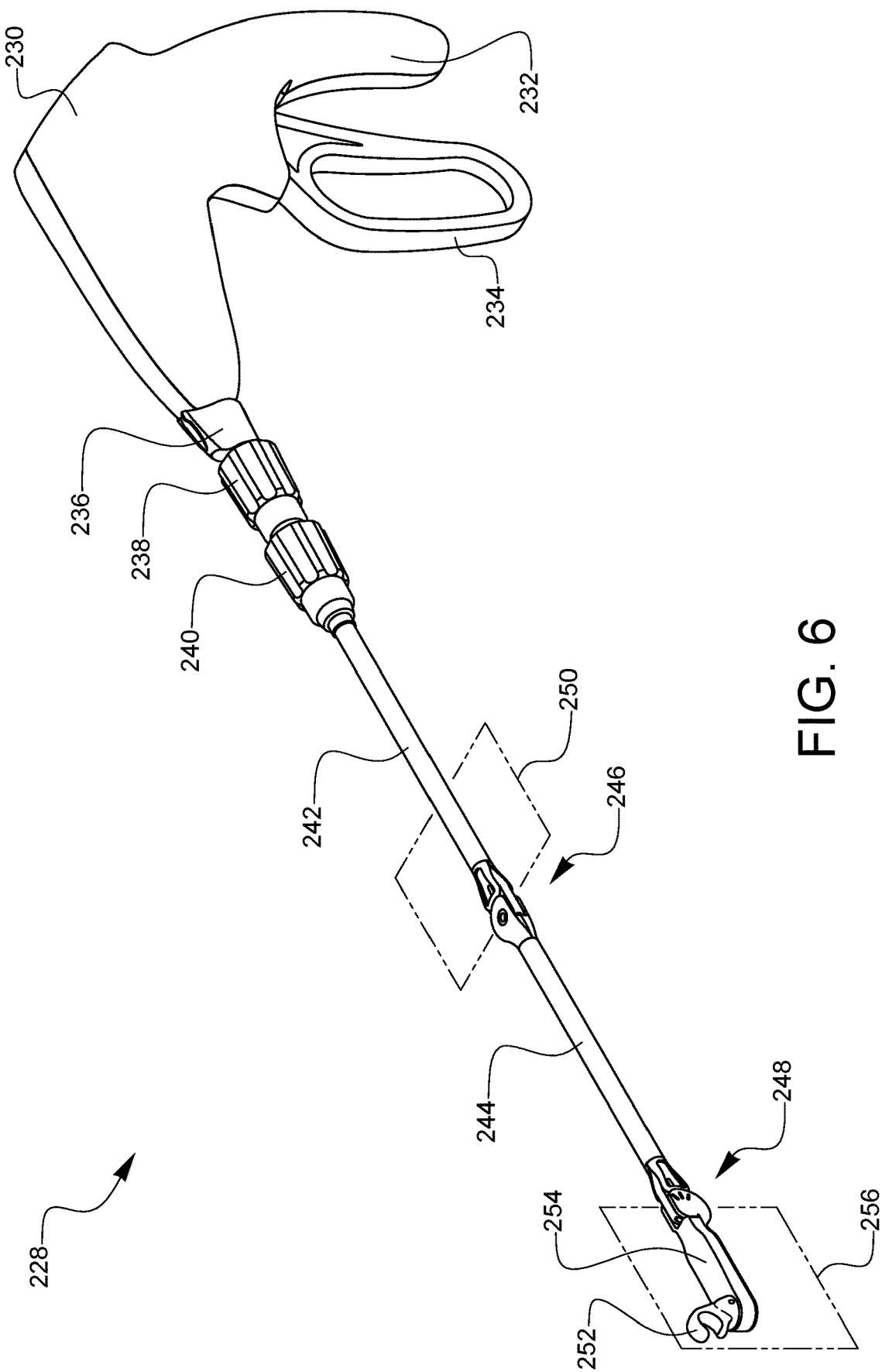
FIG. 6 is a top-left-front perspective view of another embodiment of a minimally invasive surgical device.

FIG. 6 is a top-left-front perspective view of another embodiment of a minimally invasive vessel harvesting device 228. The minimally invasive vessel harvesting device 228 has a housing 230 which extends down to form a handle 232. The device also has an actuation lever 234 which operates in a similar fashion as previous embodiments described herein. The minimally invasive vessel harvesting device 228 also has a shaft 242 which is coupled to the housing 230 by a rotational adapter which is not completely visible in this view, but is known to those skilled in the art. An indicator fin 236 of the rotational adapter can be seen in this view, however. The minimally invasive vessel harvesting device 228 has a distal tip housing 254 which is pivotably coupled to a distal shaft portion 244 by a second articulation joint 248. The distal tip housing has a blunt dissector 252 similar to those described previously herein. The distal shaft portion 244 is pivotably coupled to the shaft 242 by a first articulation joint 246. The first articulation joint 246 is operationally coupled to a first articulation knob 238 such that rotation of the first articulation knob 238 causes the first articulation joint 246 to articulate the distal shaft portion 244 in a first plane 250. The second articulation joint 248 is operationally coupled to a second articulation knob 240 such that rotation of the second articulation knob 240 causes the second articulation joint to articulate the distal tip housing 254 in a second plane 256. In this example, the first plane 250 is substantially perpendicular to the second plane 256. In other embodiments having two articulation joints, the two articulation planes may not be substantially parallel. Other embodiments may have more or fewer, including none, articulation joints. The articulation joints in other embodiments may be capable of movement in more than one plane. Embodiments of rotation adapters and minimally invasive surgical devices are known to those skilled in the art.

Figure 7:
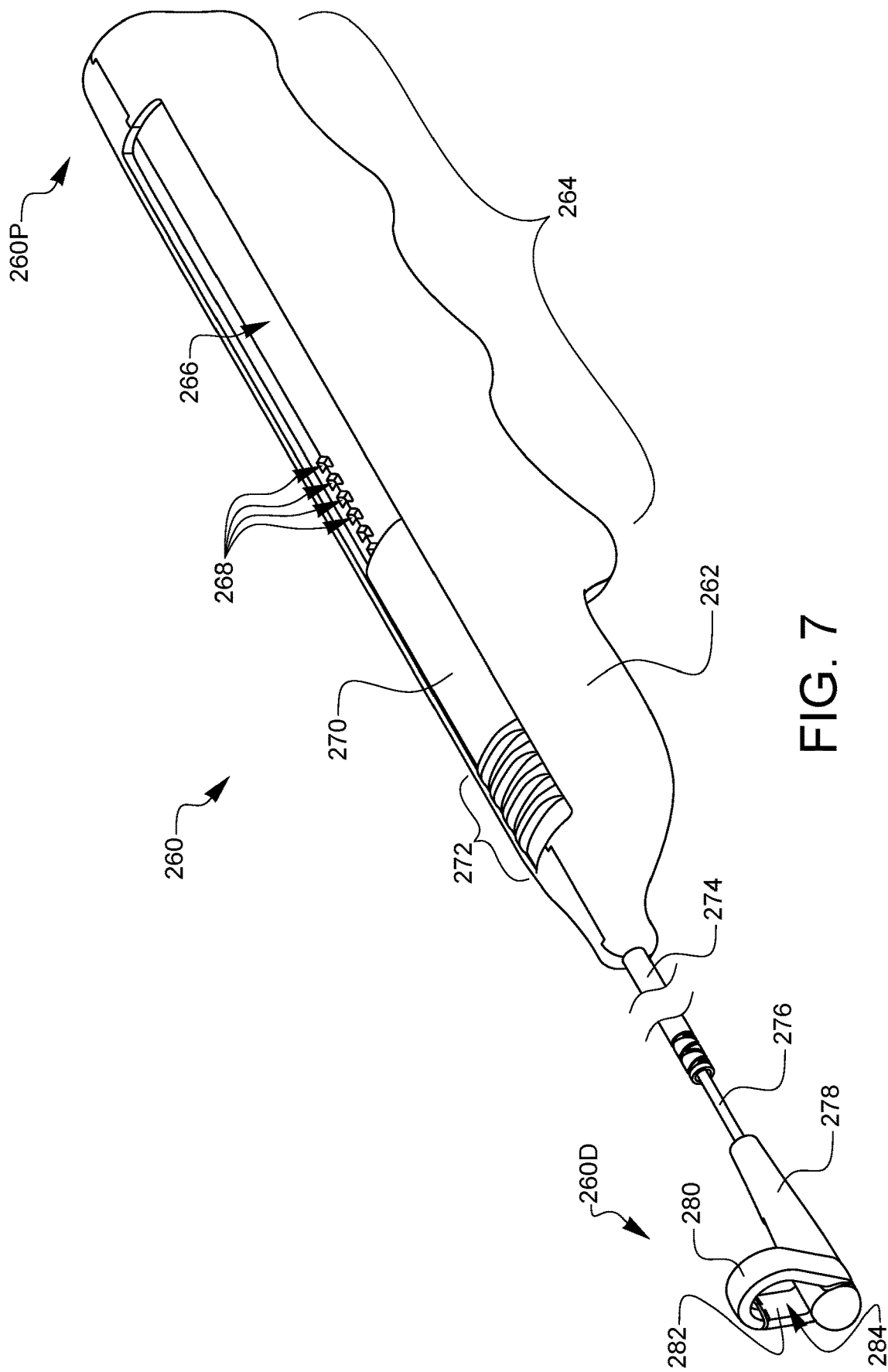
FIG. 7 is a top-left-front perspective of another embodiment of a minimally invasive surgical device.

FIG. 7 is a top-left-front perspective of another embodiment of a minimally invasive surgical device. The minimally invasive vessel harvesting device 260 has a housing 262 which forms an ergonomic handle 264. The device also has a channel 266 which is configured to provide a path for a sliding member 270 to slide longitudinally along the device 260 from its distal end 260D to its proximal end 260P. The channel 266 also defines several positioning recesses 268 which correspond to mating features on the sliding member 270. This aspect of the design provides a means to slide the sliding member 270 along the channel 260, while locking the position of the sliding member 270 if desired. The minimally invasive vessel harvesting device 260 also has a shaft 274 which is coupled to the housing 262. The shaft 274 extends towards the distal end 260D of the minimally invasive vessel harvesting device 260 and has a secondary shaft 276 coupled to the shaft 274. Coupled to the secondary shaft 276 is a distal tip 278 which defines a u-shaped or protuberant, arcuate finger 280 extending in an arcuate fashion. The arcuate curvature of the finger 280 is formed in a direction substantially perpendicular to the distal tip 278 and perpendicular to the shaft 274 and secondary shaft 276 and may be considered as and used as a blunt dissector. While the arcuate finger 280 does not close at both ends in contact with the distal tip 278, a gliding member 282 provides such a closure. The gliding member 282 is coupled to the sliding member 270 and configured such that when the sliding member 270 is moved towards the proximal end 260P, the gliding member 282 also moves towards the proximal end 260P of the minimally invasive vessel harvesting device 260. When the gliding member 282 moves in a direction towards the proximal end 260P of the minimally invasive vessel harvesting device 260, the arcuate finger 280 is open. This open position allows for the minimally invasive vessel harvesting device 260 to be placed around a vessel such as an IMA to place the arcuate finger 280 around the vessel during a harvesting or takedown procedure. When the gliding member 282 moves in a direction towards the distal end 260D of the minimally invasive vessel harvesting device 260, the arcuate finger 280 is in a position that in combination with the position of the arcuate finger 280 forms a closed loop. This closed loop position allows for the operator of the minimally invasive vessel harvesting device 260 to hold or secure a vessel such as an IMA in place within the closed loop formed by the gliding member 282 and the arcuate finger 280 during a harvesting or takedown procedure. In other embodiments the loop formed by the gliding member 282 and the arcuate finger 280 may be substantially parallel to the shaft 274 of the minimally invasive vessel harvesting device 260, or at a position somewhere between substantially parallel and substantially perpendicular. Other embodiments may not form an arcuate loop and may form closures or loops of differing shapes.

Figure 8:
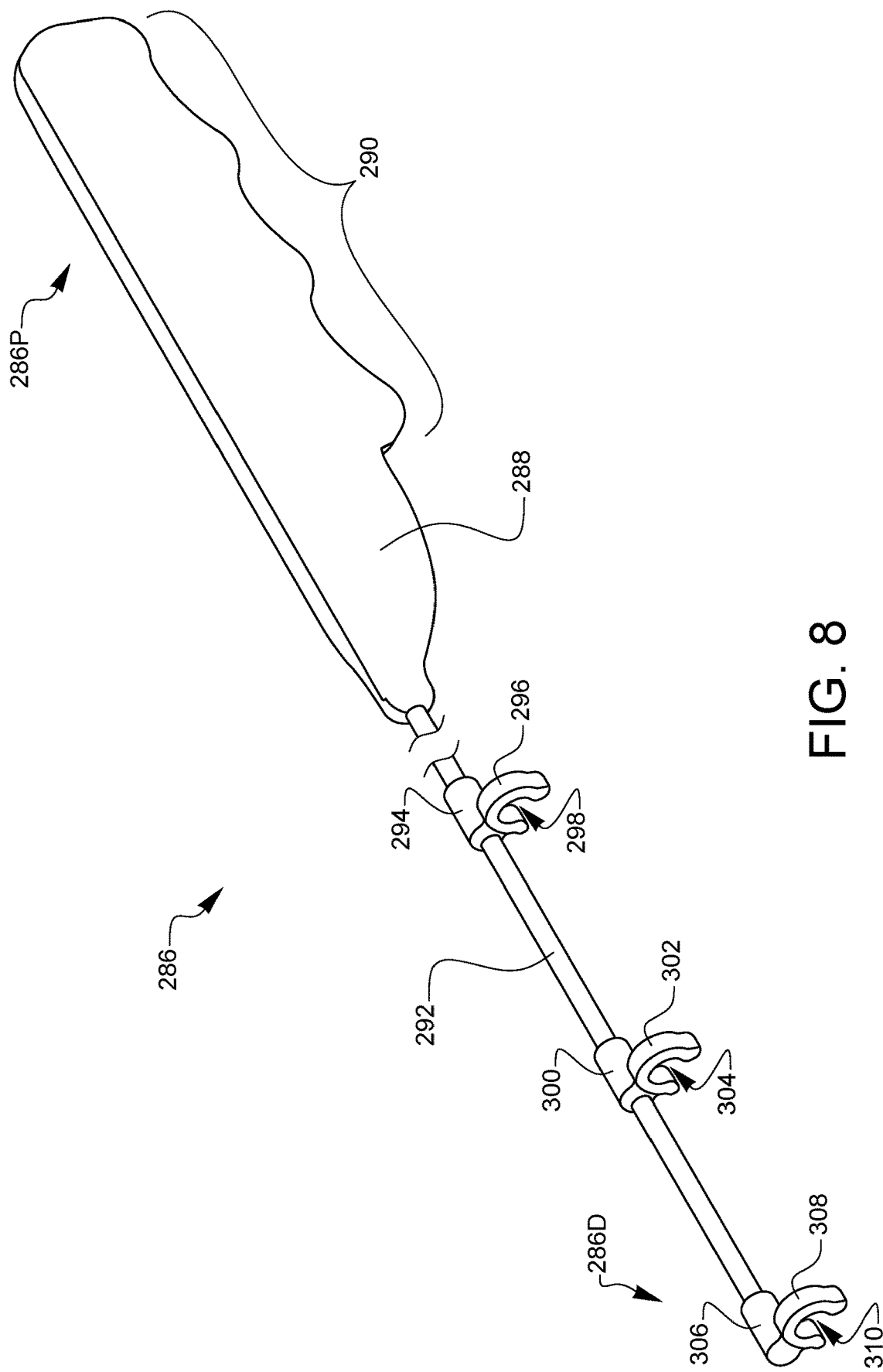
FIG. 8 is a top-left-front perspective of another embodiment of a minimally invasive surgical device.

FIG. 8 is a top-left-front perspective of another embodiment of a minimally invasive surgical device. The minimally invasive vessel harvesting device 286 has a housing 288 which forms an ergonomic handle 290. The minimally invasive vessel harvesting device 286 also has a shaft 292 which is coupled to the 288. The shaft 292 extends towards the distal end 286D of the minimally invasive vessel harvesting device 286. Coupled to the shaft 292 are several arcuate shaped blunt dissectors or omega-shaped fingers 296, 302, 308. These are referred to as omega-shaped due to their similarity to the Greek letter omega. They may also be referred to as c-shaped or u-shaped. The arcuate curvature of the fingers 296, 302, 308 are formed in a direction substantially perpendicular to the shaft. A first omega-shaped finger 296 is coupled to the shaft 292 by a first tubular mount 294 and defines an opening 298. A second omega-shaped finger 302 is coupled to the shaft 292 by a tubular mount 300 and defines an opening 304. A third omega-shaped finger 308 is coupled to the shaft 292 by a tubular mount 306 and defines an opening 310. The openings 298, 304, 310 formed by each of the omega-shaped fingers 296, 302, 308 allows for the minimally invasive vessel harvesting device 286 to be placed around a vessel such as an IMA in one or more locations to place one or more of the omega-shaped fingers 296, 302, 308 around the vessel during a harvesting or takedown procedure to temporarily hold or secure the vessel in a desired placement or position. In other embodiments the opening formed by the fingers 296, 302, 308 may be substantially parallel to the shaft 292 of the minimally invasive vessel harvesting device 286, or at a position somewhere between substantially parallel and substantially perpendicular. Other embodiments of fingers may not form an arcuate loop and may form closures or loops of differing shapes.

Figure 9:
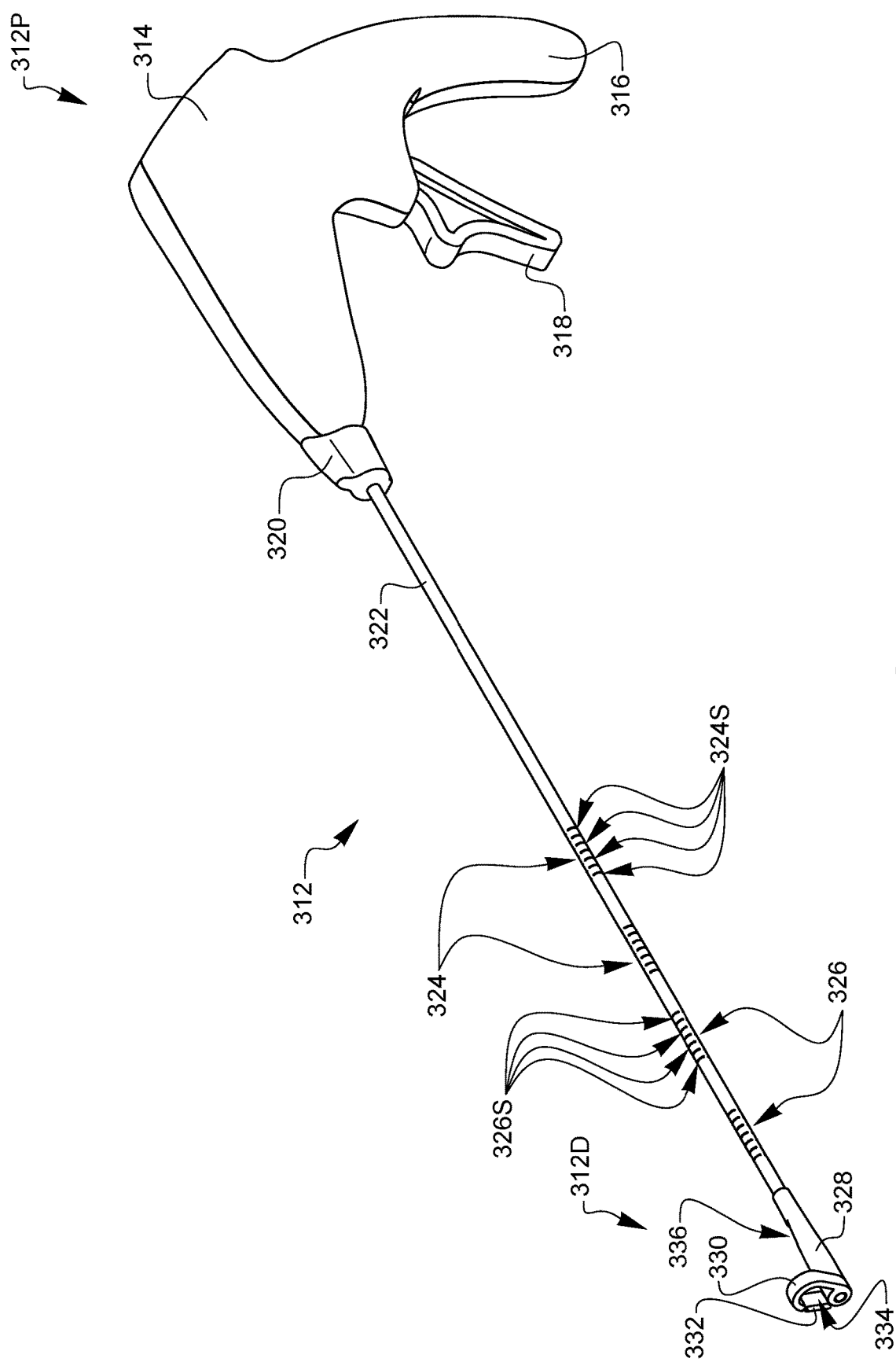
FIG. 9 is a top-left-front perspective of another embodiment of a minimally invasive surgical device.

FIG. 9 is a top-left-front perspective of another embodiment of a minimally invasive surgical device. The minimally invasive vessel harvesting device 312 has a housing 314 at a proximal end 312P, the housing forming an ergonomic handle 316. The device 312 also has an articulation lever 318 disposed within the housing 314 and a rotation adaptor knob 320. The rotation adaptor knob 320 can be rotated around a longitudinal axis of an attached shaft 322 to enable rotatable positioning of the shaft 322 and therefore a distal end 312D of the device 312. The hollow shaft 322 is mounted onto the rotation adaptor knob 320 and contains a rigid rod or drive wire which is not visible here but will be described later in more detail. Along the shaft 322, closer to the housing 314, is a first plurality of horizontal articulation joints 324 each composed of several slits 324S. Further towards the distal end 312D of the device 312, also located along the shaft 322, is a second plurality of vertical articulation joints 326 each composed of several slits 326S. The first plurality of articulation joints 324 articulate in a plane substantially perpendicular to or substantially horizontal in relation to a plane bisecting the housing 314 or in line with the lever 318. The second plurality of articulation joints 326 articulate in a plane substantially parallel to or substantially vertical in relation to a plane bisecting the housing 314. These articulation joints 324, 326 are constructed of slits 324S, 326S in the desired direction of articulation. It should be noted that upon rotation of the rotation adaptor knob 320 this aforementioned relationship of the direction of articulation between the shaft 322 and the directions of articulation become offset by the amount of rotation. In the case of the embodiment shown in FIG. 9, each partial rotation of the rotation adaptor knob 320 rotates the shaft 322 sixty degrees about a longitudinal axis defined by the shaft 322, although alternate embodiments may have different extents of partial rotation. Alternate embodiments of an articulating shaft 322 may include varying numbers of slits, for example, from about 1 to about 10, from about 3 to about 8, or from about 5 to about 7. The slits 324S, 326S are defined by partial circumferential segmentation of the outer surface of the hollow rigid shaft 322. While the articulation feature in this embodiment consists of multiple slits for each joint, the articulation feature in alternate embodiments may also include other articulating joint constructions configured to be similarly positioned, such as hinges, flexible shaft materials, and other types of articulating joint construction known to those skilled in the art, and will also be configured such that the shaft 322 can be formed into a desired shape or angle of approach for the surgical procedure, and will remain in the set configuration until intentionally moved to a different shape or angle of the shaft 322. While these articulation joints 324, 326 move and are configured to be positioned in the aforementioned planes, alternate arrangements of articulation joints may be used in alternate device embodiments. For example, horizontal articulation joints may be located closer to the distal tip 328 while vertical articulation joints may be located closer to the housing 314, vertical and horizontal articulation joints may alternate along the shaft, or varying numbers of each may be present in alternate device embodiments. Further towards the distal end 312D of the device 312 is a distal tip 328 fixedly mounted onto the shaft 322. The distal tip 328 includes an arcuate finger 330 and a slidably engaged gliding member 332 which reversibly form a channel or opening 334 defined by the combination of the gliding member 332 and the arcuate finger 330 in the position shown in FIG. 9. The enclosed channel or opening 334 is configured to retain a vessel, artery, or other anatomical feature within the channel or opening 334. The vessel, artery, or other anatomical feature can be released by actuating the lever 318. As the lever 318 of the device 312 is squeezed towards the handle 316, the gliding member 332 moves along a cam path 336 defined by the distal tip 328 to open and allow entry or passage of a vessel or other anatomical feature into the channel or opening 334 defined by the distal tip 328. Further details of this movement are detailed in regard to FIGS. 10A and 10B.

Figure 10A:
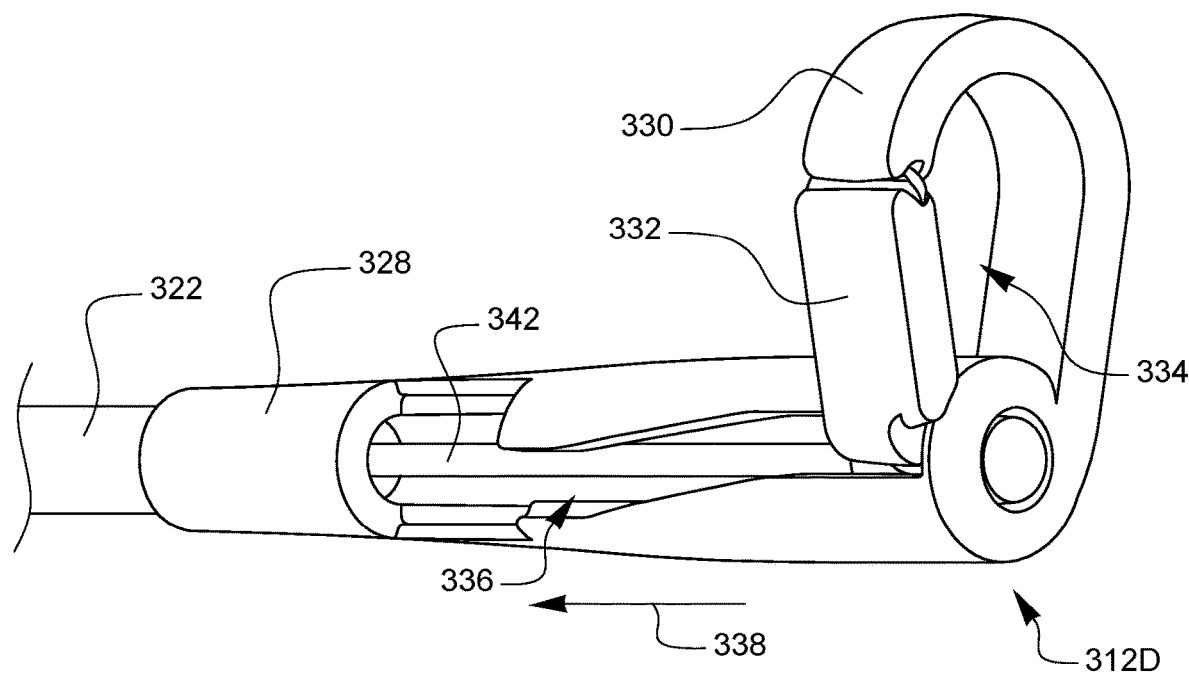
FIGS. 10A-10B are side partial cross-sectional views of a distal end of the minimally invasive surgical device of FIG. 9, illustrating a closed and opened position, respectively.
Figure 10B:
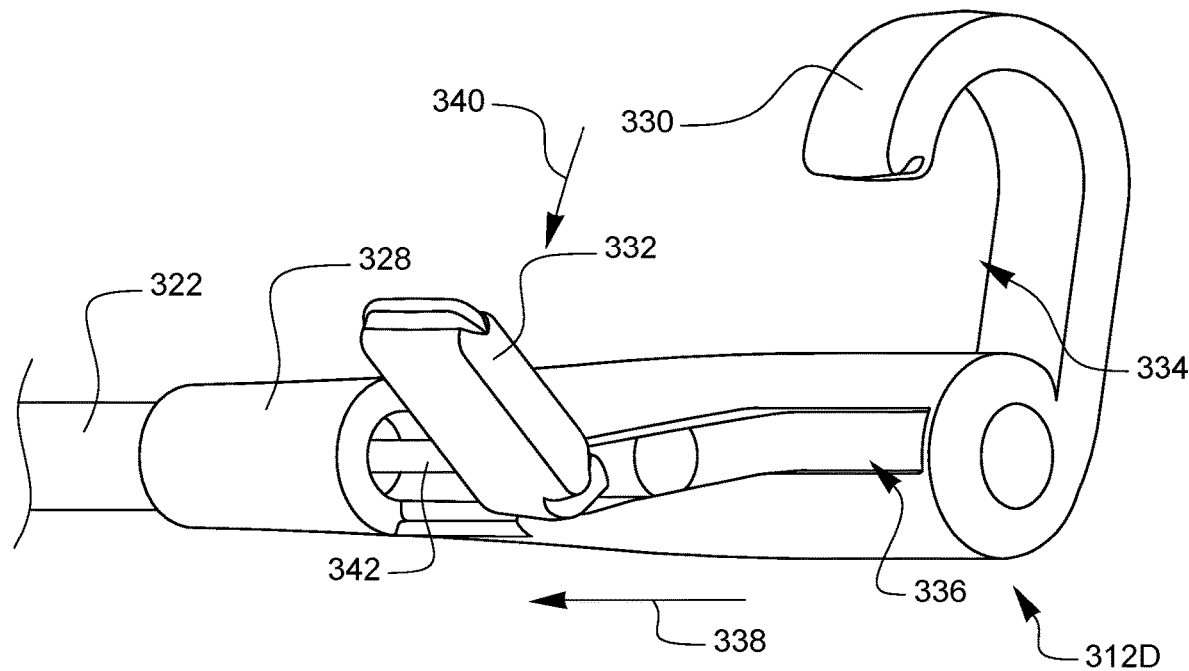

FIGS. 10A-10B are side partial cross-sectional views of a distal end of the minimally invasive surgical device of FIG. 9, illustrating a closed and opened position, respectively.

FIG. 10A illustrates the arrangement of the distal tip 328 when the lever 318 of the device 312 is in the unsqueezed position, with lever 318 positioned away from the handle 316. The drive wire 342 is coupled to the gliding member 332 and is fully extended towards the distal end 312D of the device 312. This arrangement maintains the gliding opening 334 at the distal tip 328 of the device 312, with the gliding member 332 and the arcuate finger 330 completing a full closure around the channel or opening 334. In this configuration, a vessel can be entrained within the opening 334 for holding or other desired surgical manipulation, for example, during a vessel harvesting minimally invasive surgical procedure. When the lever 318 is squeezed towards the handle 316 of the device 312, the drive wire 342 and also the connected gliding member 332 are caused to slide or move in direction 338, towards the proximal end 312P of the device 312.

FIG. 10B illustrates the position of the features and elements of the distal tip 328 of the device 312 once the handle 316 is squeezed towards the handle 316. As the drive wire 342 moves in direction 338, the gliding member 332 moves along with the drive wire 342 along the cam path 336 defined by the distal tip 328. The cam path 336 is configured such that the gliding member 332 rotates away from the distal tip 328 in direction 340 as the inner surface of the gliding member 332 interferes with the defined path of the cam path 336. This movement in direction 338 and substantially simultaneous rotation in direction 340 allows for additional clearance to open the opening 334 for a vessel or other anatomical feature to be placed within the opening 334 on the distal tip 328 of the device 312. When the desired anatomical feature is placed into the opening 334, the lever 318 can be released by the user of the device 312 and position of the distal tip 328 returns to the position illustrated in FIG. 10A, effectively trapping or capturing the anatomical feature securely in the opening 334 of the distal tip 328.

Figure 11:
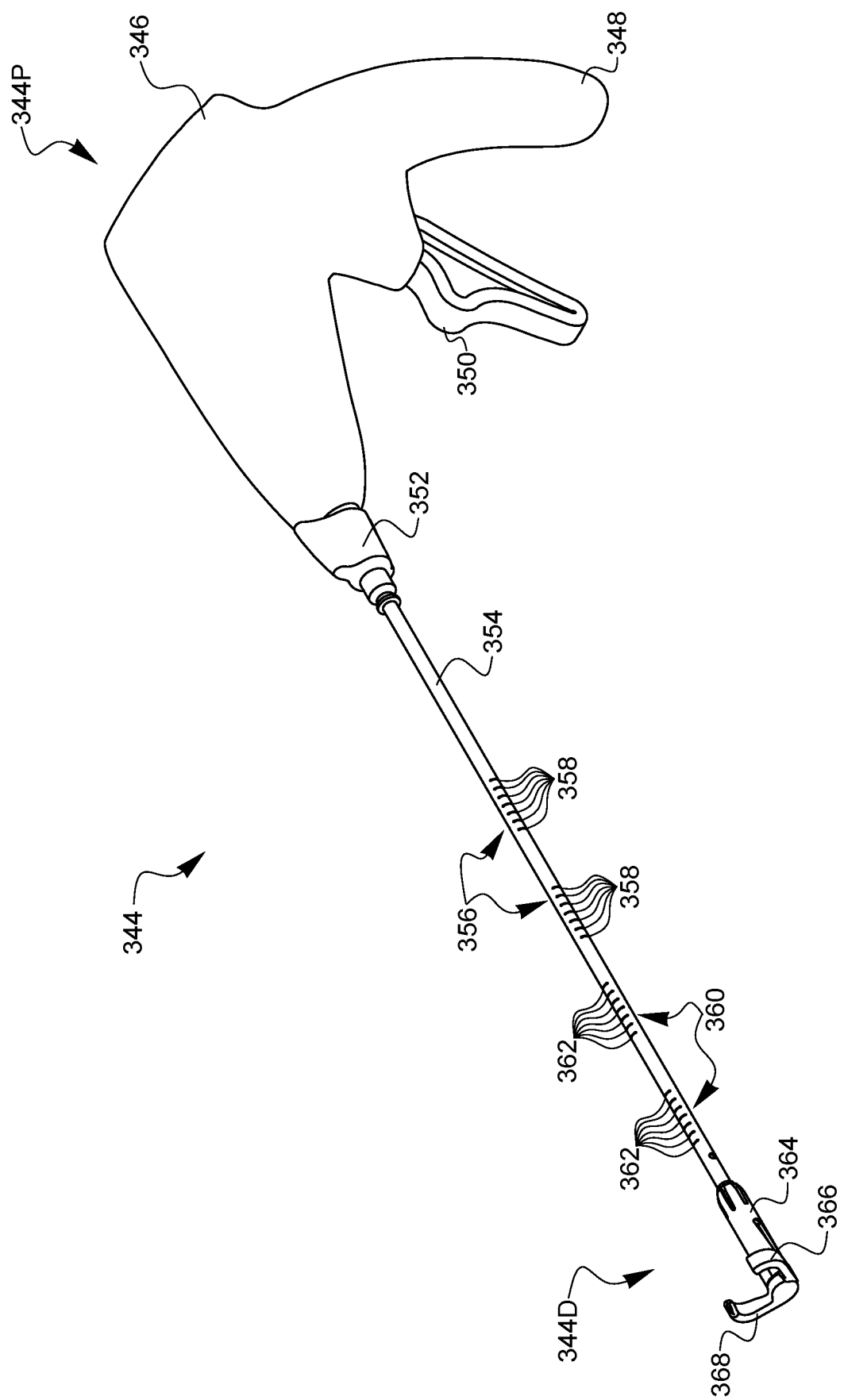
FIG. 11 is a top-left-front perspective view of another embodiment of a minimally invasive surgical device.

FIG. 11 is a top-left-front perspective view of another embodiment of a minimally invasive surgical device. The minimally invasive vessel harvesting device 344 has a housing 346 at a proximal end 344P, the housing forming an ergonomic handle 348. The device 344 also has an articulation lever 350 disposed within the housing 346 and a rotation adaptor knob 352. The rotation adaptor knob 352 can be rotated around a longitudinal axis of an attached shaft 354 to enable rotatable positioning of the shaft 354 and therefore a distal end 344D of the device 344. The hollow shaft 354 is mounted onto the rotation adaptor knob 352 and contains a drive wire which is not visible here but will be described later in more detail. Along the shaft 354, closer to the housing 346, is a first plurality of horizontal articulation joints 356 each composed of several slits 358. Further towards the distal end 344D of the device 344, also located along the shaft 354, is a second plurality of vertical articulation joints 360 each composed of several slits 362. The first plurality of articulation joints 356 articulate in a plane substantially perpendicular to or substantially horizontal in relation to a plane bisecting the housing 346 or in line with the lever 350. The second plurality of articulation joints 360 articulate in a plane substantially parallel to or substantially vertical in relation to a plane bisecting the housing 346. These articulation joints 356, 360 are constructed of slits 358, 362 in the desired direction of articulation. It should be noted that upon rotation of the rotation adaptor knob 352 this aforementioned relationship of the direction of articulation between the shaft 354 and the directions of articulation become offset by the amount of rotation. In the case of the embodiment shown in FIG. 11, each partial rotation of the rotation adaptor knob 352 rotates the shaft 354 sixty degrees about a longitudinal axis defined by the shaft 354, although alternate embodiments may have different extents of partial rotation. Alternate embodiments of an articulating shaft 354 may include varying numbers of slits, for example, from about 1 to about 10, from about 3 to about 8, or from about 5 to about 7. The slits 358, 362 are defined by partial circumferential segmentation of the outer surface of the hollow rigid shaft 354. These slits may be formed by laser cutting, machining, or other means known to those skilled in the art. While the articulation feature in this embodiment consists of multiple slits for each joint, the articulation feature in alternate embodiments may also include other articulating joint constructions configured to be similarly positioned, such as hinges, flexible shaft materials, and other types of articulating joint construction known to those skilled in the art, and will also be configured such that the shaft 354 can be formed into a desired shape or angle of approach for the surgical procedure, and will remain in the set configuration until intentionally moved to a different shape or angle of the shaft 354. While these articulation joints 356, 360 move and are configured to be positioned in the aforementioned planes, alternate arrangements of articulation joints may be used in alternate device embodiments. For example, horizontal articulation joints may be located closer to a distal housing or distal tip 364 while vertical articulation joints may be located closer to the housing 346, vertical and horizontal articulation joints may alternate along the shaft, or varying numbers of each may be present in alternate device embodiments. Further towards the distal end 344D of the device 344 is a distal tip 364 fixedly mounted onto the shaft 354. The distal tip 364 includes an arcuate first blunt dissector 366 and an arcuate second blunt dissector 368 that are in an open position. The first blunt dissector may also be referred to as an arcuate finger, and the second blunt dissector 368 may also be referred to as a fixed member or a gliding member, due to a gliding movement of the first cam portion 382 throughout a cam path. When open, as illustrated in FIG. 11, the distal tip 364 is configured to receive a vessel, artery, or other anatomical feature within the distal tip 364 when the distal tip 364 is closed. The vessel, artery, or other anatomical feature can be retained and releasably held by actuating the lever 350 and placing the first blunt dissector 366 and the second blunt dissector 368 into a closed position. Further details of this operational movement are detailed in regard to FIGS. 13A-13B and 14A and 14B.

Figure 12:
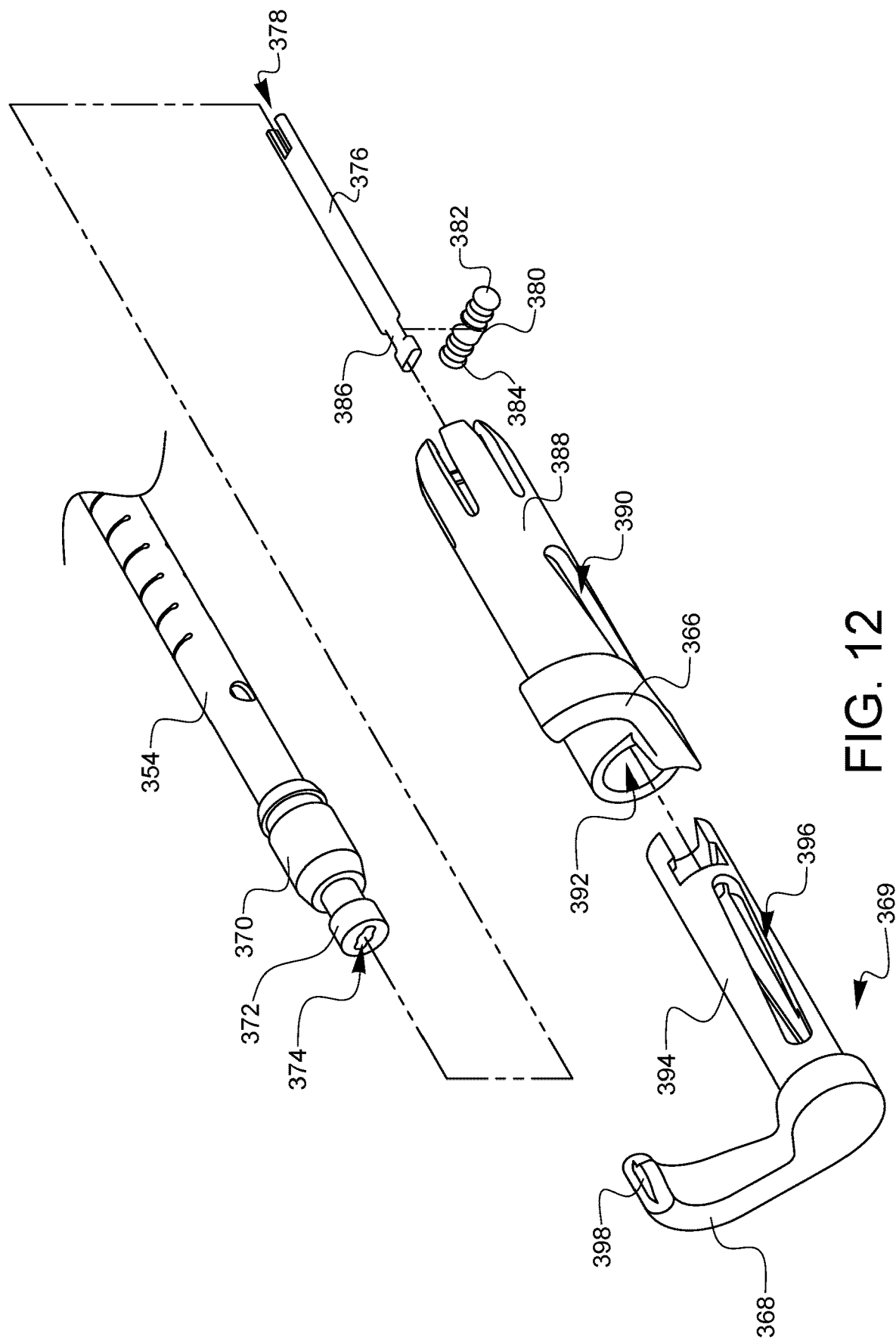
FIG. 12 is an exploded view of a distal end of the minimally invasive surgical device of FIG. 11.

FIG. 12 is an exploded view of a distal end of the minimally invasive surgical device of FIG. 11. The hollow shaft 354 is shown, having a tip 370 fixedly attached to the hollow shaft 354, further defining a head 372 and a keyway 374. A flat tip key 376 having a drive coupler 378 and an actuator coupler 386 is inserted into the keyway 374 on the tip 370. The flat tip key 376 is coupled to the drive wire, which is not shown in this view. An actuator pin 380, further defining a first cam portion 382 and a second cam portion 384 is attached to the actuator coupler 386 on the flat tip key 376. Next, a first guide tip portion body 388 which defines a first cam path 390, a channel 392, and the first blunt dissector 366 is placed over the tip 370 on the hollow shaft 354. A second guide tip portion body 394, which defines an inner cam path 396, and the second blunt dissector 368 having a is then placed inside the first guide tip portion body 388, completing the distal tip 364 assembly.

Figure 13A:
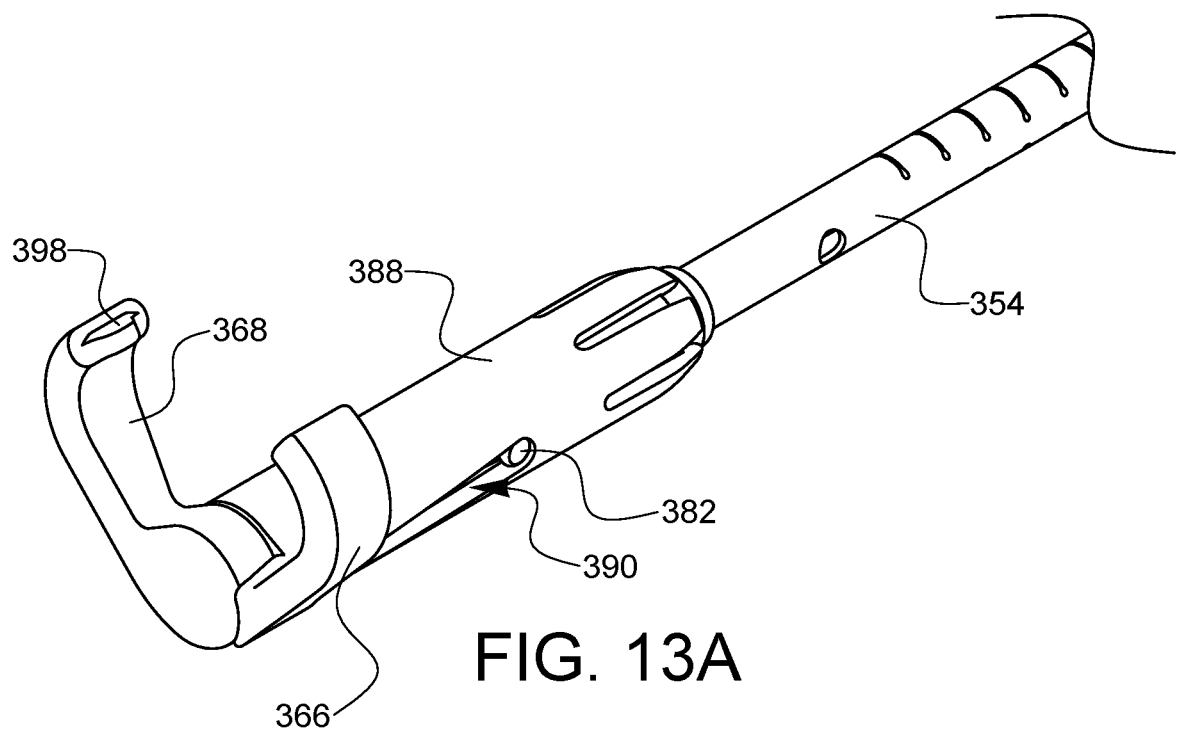
FIGS. 13A and 13B are top-left-front perspective views focused on an assembled distal end of the minimally invasive surgical device of FIG. 11 in an open and closed position, respectively.
Figure 13B:
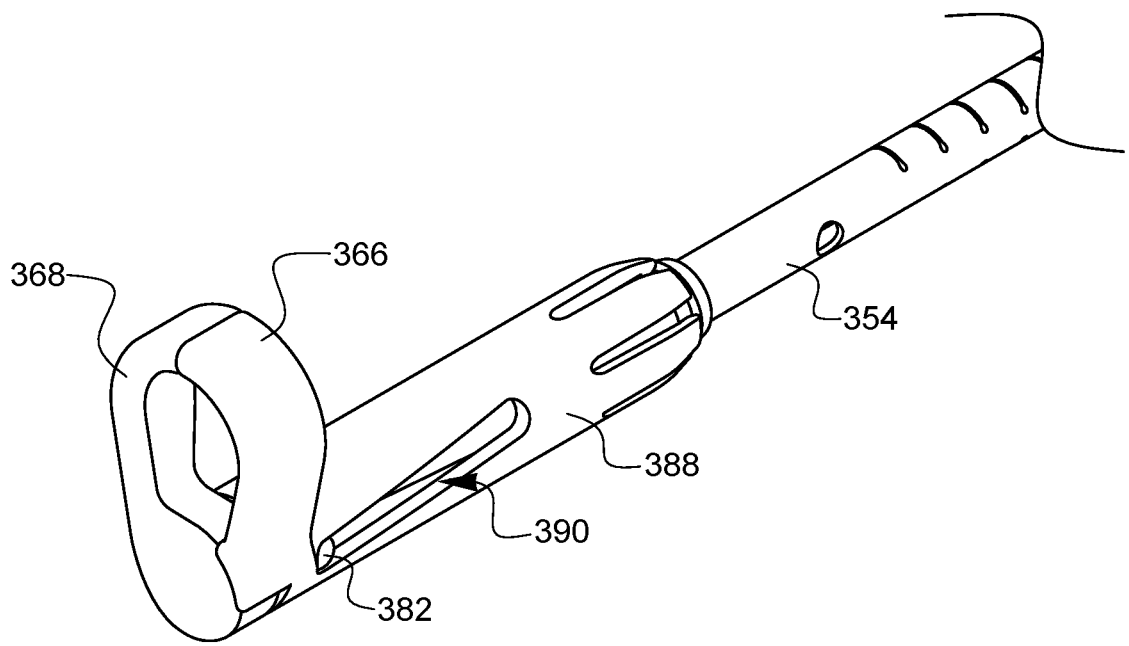

FIGS. 13A and 13B are top-left-front perspective views focused on an assembled distal end of the minimally invasive surgical device of FIG. 11 in an open and closed position, respectively. When the minimally invasive device is at rest, the relative positions of second blunt dissector 368 and first blunt dissector 366 are in an open position, and the first cam portion 382 is located closer to the hollow shaft 354 within the first cam path 390 on the first guide tip portion body 388. There may be a corresponding cam path on the opposite side of the first guide tip portion body 388 which is not shown in this view. The corresponding cam path may just be a straight path, rather than the curved path of the first cam path 390. The second blunt dissector 368 has a guiding feature 398 that seats within a corresponding recess (not shown) on the first blunt dissector 366. FIG. 13B shows the first blunt dissector 366 and second blunt dissector 368 in a closed position. Once the actuation lever is squeezed, the drive wire pushed distally, and the first cam portion 382 engaged in a distal direction away from the shaft within the first cam path 390, the first blunt dissector 366 and second blunt dissector 368 are in a closed position. This operating function will be further discussed in regard to FIGS. 14A and 14B.

FIGS. 14A and 14B are a side cross-sectional view and front-end view, respectively, of the minimally invasive surgical device of FIG. 11 in an open position. Within the housing 346 of the device 344, a spring 402 is shown providing a bias on the actuation lever 350 while the device 344 is in an open position or a position in which the actuation lever 350 has not been actuated. Also visible are the drive wire 400 coupled to a ball end 406 captured in a lever coupler 404 within the actuation lever 350. FIG. 14B is a front-end view showing the position of the first blunt dissector 366, second blunt dissector 368, and guiding feature 398 while the device 344 is in the open position. In this position, the device 344 is configured to receive a vessel, artery, or other anatomical feature within the opposing pincers, or first blunt dissector 366 and second blunt dissector 368.

FIGS. 15A and 15B are a side cross-sectional view and front-end view, respectively, of the minimally invasive surgical device of FIG. 11 in a closed position. As the actuation lever 350 of the device 344 is squeezed or actuated towards the handle in direction 408, the drive wire 400 is moved in a direction 410 towards the distal end of the device 344. As previously described in regard to FIGS. 13A and 13B, as the drive wire 400 and first cam portion 382 are coupled, the movable second blunt dissector 368 is pushed closed relative to the fixed first blunt dissector 366 along first cam path 390, where in the closed position, the device 344 may be used to hold onto and gently grasp a vessel, artery, or other anatomical feature within the closed structure defined by the first blunt dissector 366 and second blunt dissector 368.

Figure 16:
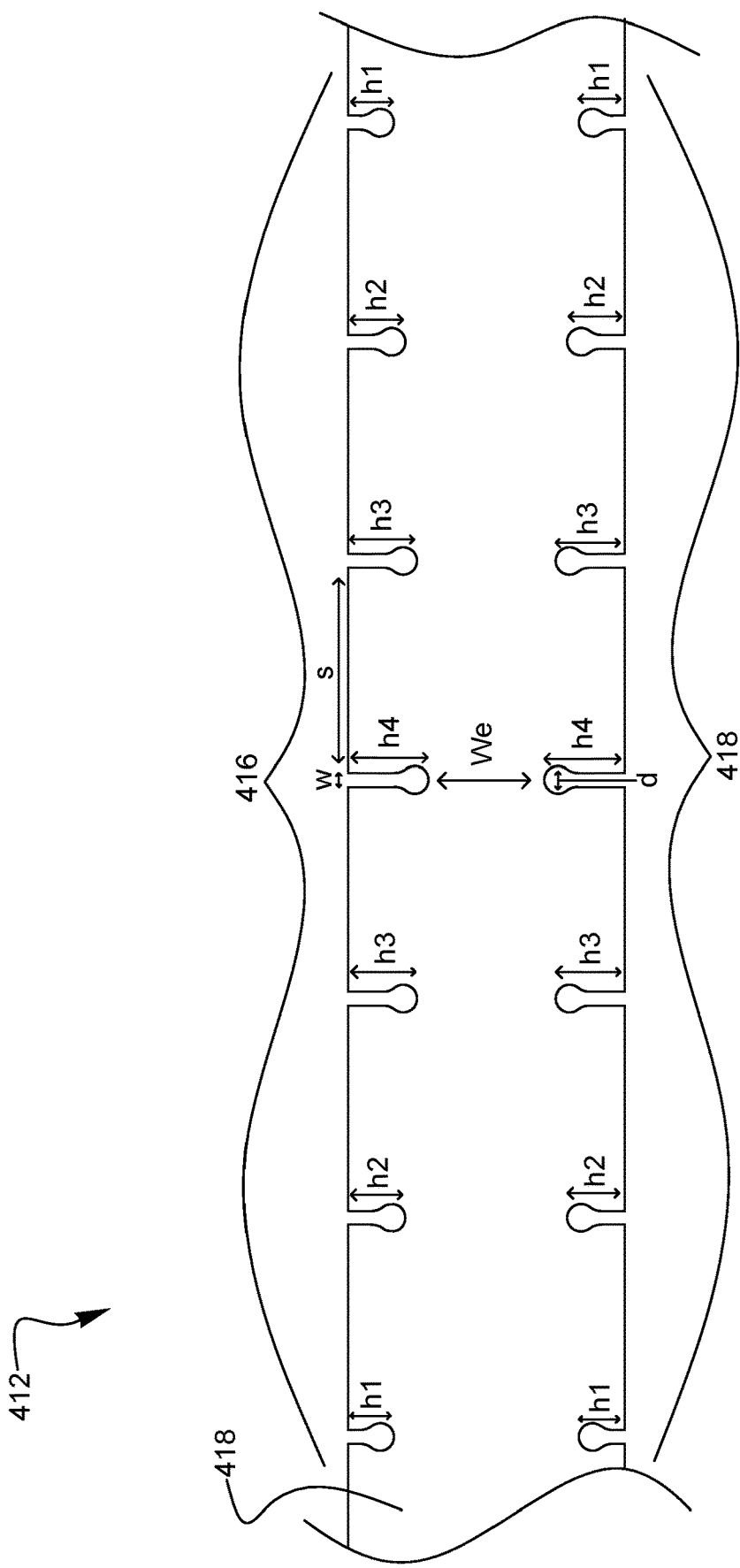
FIG. 16 is an enlarged side view of a portion of the shaft of the minimally invasive surgical device of FIG. 11.

FIG. 16 is an enlarged side view of a portion of the shaft of the minimally invasive surgical device of FIG. 11. FIG. 16 shows an enlarged side view highlighting a hollow shaft 414 having a first set of slits 412 which includes a first plurality of slits 416 and a second plurality of slits 418. The hollow rod or shaft 414 has a length and an outer circumference. The first set of slits includes a first plurality of slits across the outer circumference dissecting an apex of the hollow rod and a second plurality of slits oriented 180 degrees around the outer circumference of the hollow rod relative to the first plurality of slits. Each of the slits illustrated in FIG. 16 are made of a cross-sectional compound shape incorporating a rectangular portion and a circular portion. The rectangular portion is in communication with the outer circumference of the hollow rod. Other embodiments may incorporate slits having alternate compound shapes or alternate orientations of respective portions of compound shapes, such as triangles, squares, and other multi-sided polygons to form a variety of compound shapes.

Several parameters are notated in FIG. 16, designating important dimensional considerations relative to the slit geometry and arrangement. Diameter, d, of the circular portion of the slit, and cross-sectional height, h, of each slit is notated. As several heights are shown, h1, h2, h3, h4, they are separately designated. The heights in each of the first plurality of slits 416 and a second plurality of slits 418 illustrated in FIG. 16 show an arched or parabolic arrangement as formed by the plurality of adjacent slits. Other embodiments may have different shaped arches or arcs or may be of equivalent heights with respect to adjacent slits. The width, w, of the rectangular portion of each slit is designated, as is the spacing, s, between each slit. Lastly, the web distance, We, the distance between the circular portion or inner boundary of each of the first plurality of slits 416 and the inner boundary or circular portion of each of the second plurality of slits is indicated in FIG. 16. The diameter, d, of the circular portion is believed to influence the stress induced on the hollow shaft when bending. The circular portion is considered to reduce stress concentrations during multiple bending operations while articulating the shaft multiple times during the use of an instrument. Larger diameter circles may reduce the stresses induced while bending as compared to smaller diameter circles. The cross-sectional height—h1, h2, h3, h4—of the slit is inversely proportional to the web distance, We, and the balance between height and web distance may provide a tradeoff in the operation and performance of the instrument shaft between bendability and yield strength. This particular arrangement provides an instrument shaft configured to yield under bending stresses without breaking. When We is larger more stress can be accommodated by the instrument shaft under bending stress, and when We is smaller, less stress can be accommodated by the instrument shaft under bending stress. Height, h, width, w, and spacing between slits, s, influence the bend angle and bending radius of the portion of the hollow instrument shaft that includes a set of slits. Reduced dimensions in h, w, and s will provide a tighter bend radius, and vice versa. It should be noted that regardless of the relative dimensions and arrangements of each of the aforementioned parameters illustrated in FIG. 16, that each of the slits may have differing values of each of the aforementioned parameters in alternate embodiments of an articulatable instrument shaft. This combination of parameters and features as described can be combined to provide an articulatable instrument shaft that has rigidity, malleability, and robustness that can be articulate and bent, hold its shape, and be repeatedly manipulated during the course of a minimally invasive surgical procedure. As shown in FIG. 11, for example, an instrument shaft may have multiple sets of slits having similar features as described previously, such as a second set of slits, or a third or fourth set of slits, or more. These multiple sets of slits may be all oriented similarly, or as in the example from FIG. 11, the multiple sets of slits are perpendicular to one another, for example, a second set of slits is oriented 90 degrees around the outer circumference of the hollow rod relative to the first plurality of slits. Additionally, alternate embodiments may have only one set of slits or may be oriented 180 degrees apart or of varying angles depending on application considerations. Furthermore, slits may have alternate shapes—such as triangular, circular, polygonal—alternate compound shapes—such as dog bone, mushroom, or hot dog-shaped—and alternate dimensions as compared to those characterized and defined herein. Overall shaft diameter also plays a role and interacts with each of the features defined previously, and presumably would have to be modified or scaled proportionally for differing shaft diameters.

Various advantages of a device for vessel harvesting have been discussed above. Embodiments discussed herein have been described by way of example in this specification. It will be apparent to those skilled in the art that the foregoing detailed disclosure is intended to be presented by way of example only, and is not limiting. As just one example, although the end effectors in the discussed examples were often focused on the use of a scope, such systems could be used to position other types of surgical equipment. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A minimally invasive surgical device comprising:
   a housing;
   an actuator coupled to a first portion of the housing;
   a shaft extending along a longitudinal axis from a proximal end to a distal end, wherein a first portion of the shaft is coupled to a second portion of the housing; and
   a distal tip assembly comprising:
      a distal tip housing fixedly coupled to the distal end of the shaft;
      a first blunt dissector rotatably coupled to the distal tip housing, wherein the first blunt dissector is operably coupled to the actuator by a drive wire that is elongated and extends from a proximal end to a distal end, the proximal end of the drive wire being coupled to a portion of the actuator and at least a portion of the drive wire extends through an interior portion of the shaft; and
      a second blunt dissector coupled to the distal tip housing;
   wherein the first blunt dissector is operably coupled to the actuator such that when the actuator is in a first position, the first blunt dissector is in a first rotational position relative to the distal tip housing, and when the actuator is in a second position, the first blunt dissector is in a second rotational position relative to the distal tip housing,
   wherein the distal end of the drive wire is coupled to a first cam portion that is received into a first cam path formed in a guide tip portion body that is fixedly coupled to the first blunt dissector such that as the actuator is displaced from the first position to the second position, the first cam portion is displaced in a direction along the longitudinal axis of the shaft within the first cam path to rotate the guide tip portion body fixedly coupled to the first blunt dissector, and
   wherein the first blunt dissector is configured to rotate about a tip axis that is aligned with or parallel to the longitudinal axis at the distal end of the shaft.

2. The minimally invasive surgical device of claim 1, wherein the second blunt dissector is rotatably coupled to the distal tip housing, the second blunt dissector being operably coupled to the actuator such that when the actuator is in the first position, the second blunt dissector is in a first rotational position relative to the distal tip housing, and when the actuator is in the second position, the second blunt dissector is in a second rotational position relative to the distal tip housing.

3. The minimally invasive surgical device of claim 2, wherein the second blunt dissector is configured to rotate about the tip axis.

4. The minimally invasive surgical device of claim 1, wherein the shaft is rotatably coupled to the second portion of the housing such that the first portion of the shaft is configured to rotate about the longitudinal axis.

5. The minimally invasive surgical device of claim 1, wherein the longitudinal axis is linear from the distal end of the shaft to the proximal end of the shaft.

6. The minimally invasive surgical device of claim 1, wherein the second blunt dissector is fixed relative to the distal tip housing.

7. The minimally invasive surgical device of claim 1, wherein the actuator comprises a lever that is pivotably coupled to the first portion of the housing such that the lever pivots from the first position to the second position, and wherein the first portion of the shaft is at or adjacent to the proximal end of the shaft.

8. The minimally invasive surgical device of claim 1, further comprising:
   a first plurality of slits formed in a second portion of the shaft, wherein all or a portion of the first plurality of slits cooperate to allow the second portion of the shaft to bend such that a portion of the longitudinal axis extending along the second portion of the shaft is not linear; and
   a second plurality of slits formed in a third portion of the shaft, wherein all or a portion of the second plurality of slits cooperate to allow the third portion of the shaft to bend such that a portion of the longitudinal axis extending along the second portion of the shaft is not linear.

9. The minimally invasive surgical device of claim 8, wherein each of the first plurality of slits extends from a first end to a second end in a direction normal to the longitudinal axis of the shaft, and each of the second plurality of slits extends from a first end to a second end in a direction normal to the longitudinal axis of the shaft.

10. The minimally invasive surgical device of claim 9, wherein the first end of each of the first plurality of slits is aligned along a first reference line that is parallel to the longitudinal axis and the second end of each of the first plurality of slits is aligned along a second reference line that is parallel to the longitudinal axis,
   wherein the first end of each of the second plurality of slits is aligned along a third reference line that is parallel to the longitudinal axis and the second end of each of the second plurality of slits is aligned along a fourth reference line that is parallel to the longitudinal axis, and
   wherein the first reference line is not aligned with the third reference line and the second reference line is not aligned with the fourth reference line.

11. The minimally invasive surgical device of claim 1, wherein the first cam portion is a portion of an actuator pin that extends along a linear axis that is normal to the tip axis.

12. The minimally invasive surgical device of claim 11, wherein the actuator pin does not rotate about the tip axis relative to the distal tip housing.

13. The minimally invasive surgical device of claim 1, wherein the distal tip housing includes a tip portion fixedly attached to the distal end of the shaft, the tip portion having an aperture that extends through the tip portion from a proximal end of the tip portion to a distal end of the tip portion.

14. The minimally invasive surgical device of claim 1, wherein the guide tip portion body is integrally formed with the first blunt dissector.

15. The minimally invasive surgical device of claim 1, wherein the distal end of the drive wire is coupled to a second cam portion that is received into a second cam path formed in a second guide tip portion body that is fixedly coupled to the second blunt dissector such that as the actuator is displaced from the first position to the second position, the second cam portion is displaced in a direction along the longitudinal axis of the shaft within the second cam path to rotate the second guide tip portion body fixedly coupled to the second blunt dissector.

16. The minimally invasive surgical device of claim 15, wherein the second guide tip portion body is integrally formed with the second blunt dissector.

17. The minimally invasive surgical device of claim 15, wherein the first cam portion is a first portion of a cylindrical member and second cam portion is a second portion of the cylindrical member.

18. A minimally invasive surgical device comprising:
a housing;
an actuator coupled to a first portion of the housing;
a shaft extending along a longitudinal axis from a proximal end to a distal end, wherein a first portion of the shaft is rotatably coupled to a second portion of the housing such that the first portion of the shaft is configured to rotate about the longitudinal axis relative to the second portion of the housing;
a first plurality of slits formed in a second portion of the shaft, wherein all or a portion of the first plurality of slits cooperate to allow the second portion of the shaft to bend such that a portion of the longitudinal axis extending along the second portion of the shaft is not linear;
a second plurality of slits formed in a third portion of the shaft, wherein all or a portion of the second plurality of slits cooperate to allow the third portion of the shaft to bend such that a portion of the longitudinal axis extending along the second portion of the shaft is not linear; and a distal tip assembly comprising:
a distal tip housing fixedly coupled to the distal end of the shaft;
a first blunt dissector rotatably coupled to the distal tip housing, wherein the first blunt dissector is operably coupled to the actuator by a drive wire that is elongated and extends from a proximal end to a distal end, the proximal end of the drive wire being coupled to a portion of the actuator and at least a portion of the drive wire extends through an interior portion of the shaft; and
a second blunt dissector rotatably coupled to the distal tip housing,
wherein each of the first blunt dissector and the second blunt dissector is operably coupled to the actuator such that when the actuator is in a first position, each of the first blunt dissector and the second blunt dissector is in a first rotational position relative to the distal tip housing, and when the actuator is in a second position, each of the first blunt dissector and the second blunt dissector is in a second rotational position relative to the distal tip housing, and wherein the distal end of the drive wire is coupled to a first cam portion that is received into a first cam path formed in a guide tip portion body that is fixedly coupled to the first blunt dissector such that as the actuator is displaced from the first position to the second position, the first cam portion is displaced in a direction along the longitudinal axis of the shaft within the first cam path to rotate the guide tip portion body fixedly coupled to the first blunt dissector, and wherein each of the first blunt dissector and the second blunt dissector is configured to rotate about a tip axis that is aligned with or parallel to the longitudinal axis at the distal end of the shaft.

\* \* \* \* \*